(12) United States Patent
Sakamoto

(10) Patent No.: US 11,055,865 B2
(45) Date of Patent: Jul. 6, 2021

(54) IMAGE ACQUISITION DEVICE AND METHOD OF OPERATING IMAGE ACQUISITION DEVICE

(71) Applicant: OLYMPUS CORPORATION, Tokyo (JP)

(72) Inventor: Yohei Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 111 days.

(21) Appl. No.: 16/542,496

(22) Filed: Aug. 16, 2019

(65) Prior Publication Data

US 2020/0074655 A1 Mar. 5, 2020

(30) Foreign Application Priority Data

Aug. 30, 2018 (JP) .............................. JP2018-161521

(51) Int. Cl.
*G06T 7/55* (2017.01)
*G06T 15/00* (2011.01)
(Continued)

(52) U.S. Cl.
CPC ............ *G06T 7/55* (2017.01); *A61B 1/00009* (2013.01); *A61B 5/1079* (2013.01); *G06T 3/20* (2013.01);
(Continued)

(58) Field of Classification Search
CPC .. G06T 7/55; G06T 7/70; G06T 15/00; G06T 3/20; G06T 7/292; G06T 7/0012;
(Continued)

(56) References Cited

U.S. PATENT DOCUMENTS

2010/0215220 A1* 8/2010 Yamaguchi ............... G06T 7/74
382/106
2014/0340486 A1* 11/2014 Asano ....................... G06T 7/97
348/47
(Continued)

FOREIGN PATENT DOCUMENTS

| JP | H09-026547 A | 1/1997 |
|---|---|---|
| JP | 2006-187386 A | 7/2006 |
| JP | 2014-232222 A | 12/2014 |

OTHER PUBLICATIONS

Alcantarilla et al. "Enhanced Imaging Colonoscopy Facilitates Dense Motion-Based 3D Reconstruction." 35th Annual International Conference of the IEEE Engineering in Medicine and Biology Society (EMBC), Jul. 3, 2013, pp. 7346-7349 (Year: 2013).*

(Continued)

*Primary Examiner* — Jon Chang
(74) *Attorney, Agent, or Firm* — Scully, Scott, Murphy & Presser, P.C.

(57) ABSTRACT

A control unit recognizes a direction accepted by an operation unit in a case in which an image acquisition mode is set in an image acquisition device. An image acquisition condition in the image acquisition mode is defined by first information and second information. The first information represents a speed or a distance at which the imaging visual field is changed. The second information represents a timing at which images used for restoration of the three-dimensional shape are acquired. The control unit causes a visual field changing unit to change the imaging visual field at the speed in the recognized direction or change the imaging visual field by the distance in the recognized direction. The control unit acquires at least two images at the timings from an imaging unit.

15 Claims, 28 Drawing Sheets

(51) Int. Cl.
  *A61B 1/00* (2006.01)
  *G06T 7/579* (2017.01)
  *A61B 5/107* (2006.01)
  *G06T 7/70* (2017.01)
  *G06T 3/20* (2006.01)
  *G06T 7/292* (2017.01)
  *G06T 7/00* (2017.01)
  *A61B 1/04* (2006.01)
  *G02B 23/24* (2006.01)

(52) U.S. Cl.
  CPC .............. *G06T 7/292* (2017.01); *G06T 7/579* (2017.01); *G06T 7/70* (2017.01); *G06T 15/00* (2013.01); *A61B 1/04* (2013.01); *G02B 23/24* (2013.01); *G06T 7/0012* (2013.01); *G06T 2207/10016* (2013.01); *G06T 2207/10068* (2013.01)

(58) Field of Classification Search
  CPC . G06T 2207/10068; G06T 2207/10016; G06T 7/579; A61B 1/04; A61B 1/00193; A61B 1/00009; A61B 5/1079; G02B 23/24; G01B 11/24; G01N 21/8851; G01N 2021/8887
  See application file for complete search history.

(56) References Cited

U.S. PATENT DOCUMENTS

2017/0046833 A1* 2/2017 Lurie ..................... G06T 5/008
2021/0027496 A1* 1/2021 Koyama .............. H04N 13/246

OTHER PUBLICATIONS

Atze et al. "Quantitative Measurements of Soft Tissue Structures using Image-Features in Navigated Endoscopy." 5th Global Conference on Consumer Electronics, Oct. 11, 2016, 5 pages (Year: 2016).*

Zhou et al. "Synthesis of Stereoscopic Views from Monocular Endoscopic Videos." IEEE Computer Society Conference on Computer Vision and Pattern Recognition, Jun. 13, 2010, pp. 55-62 (Year: 2010).*

* cited by examiner

IMAGE ACQUISITION DEVICE AND METHOD OF OPERATING IMAGE ACQUISITION DEVICE

BACKGROUND OF THE INVENTION

Field of the Invention

The present invention relates to an image acquisition device and a method of operating an image acquisition device.

Priority is claimed on Japanese Patent Application No. 2018-161521, filed on Aug. 30, 2018, the content of which is incorporated herein by reference.

Description of Related Art

Industrial endoscope devices are used for observation and inspection for internal damage, corrosion, and the like in boilers, turbines, engines, pipes, and the like. In such endoscope devices, a plurality of types of optical adapter used for observing and inspecting various observation objects are provided. An optical adapter is mounted on a tip end part of an endoscope and is replaceable. In inspection using such an endoscope device, there is a requirement for quantitatively measuring the size of a defect and damage to a subject. In order to respond to this requirement, there are endoscopes in which a three-dimensional measurement function is installed.

Hereinafter, a sequence in which a user performs measurement in inspection using an endoscope device will be briefly described. First, the user checks whether or not there are defects or damage inside a subject using a monocular optical adapter having excellent observation performance. In a case in which defects or damage is found during inspection, and the defects or damage is determined as a measurement target, the user switches the optical adapter from the monocular optical adapter to a measurement optical adapter. A stereo optical system is mounted in the measurement optical adapter. In order to switch the optical adapter, the user pulls back the tip end of the endoscope inserted inside the subject. After the optical adapter is switched from the monocular optical adapter to the measurement optical adapter, the user inserts the tip end of the endoscope inside the subject again. After the tip end of the endoscope reaches a place of a defect or damage found through the observation using the monocular optical adapter, the user performs measurement.

In order to perform measurement, such a procedure is necessary. For this reason, an inspection time from when a defect or damage is found to when measurement is performed is long. In other words, the inspection efficiency is low. In order to resolve this, there is a requirement for installing a three-dimensional measurement function in a monocular optical adapter used for general inspection in endoscopy. As a technology for performing three-dimensional measurement using a monocular optical adapter, for example, there is a technology disclosed in Japanese Unexamined Patent Application, First Publication No. H9-26547. The technology disclosed in Japanese Unexamined Patent Application, First Publication No. H9-26547 provides a method of performing measurement by combining structure from motion and a distance measurement means. Hereinafter, structure from motion will be abbreviated to SfM. A device can restore a three-dimensional shape of a subject using a result of SfM. Hereinafter, an image acquired for performing SfM will be referred to as a measurement image.

In order to acquire a measurement image using the technology disclosed in Japanese Unexamined Patent Application, First Publication No. H9-26547, it is necessary to acquire an image captured from each of a plurality of camera viewpoints. As one specific method of changing a camera viewpoint, there is a method of changing a camera viewpoint using a bending function of the tip end of the endoscope. For example, methods of changing a camera viewpoint using a bending function and acquiring an image are disclosed in Japanese Unexamined Patent Application, First Publication No. 2006-187386 and Japanese Unexamined Patent Application, First Publication No. 2014-232222.

SUMMARY OF THE INVENTION

According to a first aspect of the present invention, an image acquisition device includes an imaging unit, a visual field changing unit, an operation unit, and a control unit. The imaging unit generates images on the basis of an optical image of a subject within an imaging visual field. The visual field changing unit changes the imaging visual field by moving at least the imaging unit. The operation unit accepts a direction in which the imaging visual field is changed from a user. The control unit recognizes the direction accepted by the operation unit in a case in which an image acquisition mode used for acquiring the images used for restoration of a three-dimensional shape of the subject is set in the image acquisition device. The control unit reads first information and second information that define image acquisition conditions in the image acquisition mode from a storage medium. The first information represents a speed at which the imaging visual field is changed or a distance by which the imaging visual field is changed. The second information represents timings at which the images used for restoration of the three-dimensional image are acquired. The control unit causes the visual field changing unit to change the imaging visual field at the speed represented by the first information in the recognized direction or change the imaging visual field by the distance represented by the first information in the recognized direction. The control unit acquires at least two of the images at the timings represented by the second information from the imaging unit. The control unit restores the three-dimensional shape using the images acquired from the imaging unit.

According to a second aspect of the present invention, in the first aspect, the images acquired from the imaging unit may include one first image and at least one second image. The control unit may detect a region that overlaps between the first image and the second image. The control unit may cause the region in the first image to be visibly distinguishable from other regions in the first image by processing the first image. The control unit may display the processed first image on a display unit.

According to a third aspect of the present invention, in the second aspect, the operation unit may accept an execution instruction of restoration of the three-dimensional shape from the user after the first image is displayed on the display unit. The control unit may restore the three-dimensional shape in a case in which the operation unit accepts the execution instruction.

According to a fourth aspect of the present invention, in the first aspect, the images acquired from the imaging unit may include one first image and at least one second image. The control unit may determine whether or not a designation point designated by the user in the first image is included in the second image. The control unit may restore the three-dimensional shape in a case in which the control unit determines that the designation point is included in the second image.

According to the fifth aspect of the present invention, in the first aspect, after acquisition of the images based on the image acquisition conditions ends, the control unit may compare a first number with a second number. The first number may represent the number of the images acquired from the imaging unit. The second number may represent the number of the images required for restoration of the three-dimensional shape and is at least two.

According to the sixth aspect of the present invention, in the fifth aspect, the control unit may select at least the second number of the images among the images acquired from the imaging unit in a case in which the first number is larger than the second number. The control unit may restore the three-dimensional shape using the selected images.

According to the seventh aspect of the present invention, in the sixth aspect, the control unit may select at least the second number of the images on the basis of a degree of overlapping between the images acquired from the imaging unit.

According to the eighth aspect of the present invention, in the sixth aspect, the control unit may select the second number of the images that include an image that has been acquired first among the images acquired from the imaging unit and include an image that has been acquired last among the images acquired from the imaging unit.

According to the ninth aspect of the present invention, in the fifth aspect, in a case in which the operation unit accepts an image acquisition end instruction from the user and the first number is smaller than the second number, the operation unit may accept a second direction in which the imaging visual field is changed from the user. The control unit may recognize the second direction accepted by the operation unit. The control unit may cause the visual field changing unit to change the imaging visual field again at the speed represented by the first information in the recognized second direction or change the imaging visual field again by the distance represented by the first information in the recognized direction. The control unit may acquire at least one of the images from the imaging unit at the timing represented by the second information after the imaging visual field is changed in the second direction.

According to the tenth aspect of the present invention, in the fifth aspect, in a case in which the operation unit accepts an image acquisition end instruction from the user and the first number is smaller than the second number, the control unit may determine a second direction in which the imaging visual field is changed on the basis of the recognized direction. The control unit may cause the visual field changing unit to change the imaging visual field at the speed represented by the first information in the determined second direction again or change the imaging visual field by the distance represented by the first information in the determined second direction again. The control unit may acquire at least one of the images from the imaging unit at the timing represented by the second information after the imaging visual field is changed in the second direction.

According to the eleventh aspect of the present invention, in the fifth aspect, the control unit may notify the user that the first number has not reached the second number in a case in which the first number is smaller than the second number.

According to the twelfth aspect of the present invention, in the first aspect, the operation unit may accept the direction by accepting a position within the imaging visual field from the user. The control unit may recognize the direction on the basis of the position accepted by the operation unit. The first information may represent the speed at which the imaging visual field is changed. The control unit may cause the visual field changing unit to change the imaging visual field at the speed represented by the first information in the recognized direction until a center of the imaging visual field coincides with the position.

According to the thirteenth aspect of the present invention, in the first aspect, the control unit may display at least one of the images acquired from the imaging unit on a display unit. The control unit may count a first number and display information representing a ratio of the first number to a second number on the display unit. The first number may represent the number of the images acquired from the imaging unit. The second number may represent the number of the images required for restoration of the three-dimensional shape and is at least two.

According to the fourteenth aspect of the present invention, in the first aspect, the control unit may generate thumbnail images by decreasing the number of pixels of the images acquired from the imaging unit. The control unit may display the thumbnail images on a display unit.

According to the fifteenth aspect of the present invention, there is provided a method of operating an image acquisition device including an imaging unit, a visual field changing unit, an operation unit, and a control unit. The imaging unit generates images on the basis of an optical image of a subject within an imaging visual field. The visual field changing unit changes the imaging visual field by moving at least the imaging unit. The operation unit accepts a direction in which the imaging visual field is changed from a user. In a first step, the control unit recognizes the direction accepted by the operation unit in a case in which an image acquisition mode used for acquiring the images used for restoration of a three-dimensional shape of the subject is set in the image acquisition device. In a second step, the control unit reads first information and second information that define image acquisition conditions in the image acquisition mode from a storage medium. The first information represents a speed at which the imaging visual field is changed or a distance by which the imaging visual field is changed. The second information represents timings at which the images used for restoration of the three-dimensional shape are acquired. In a third step, the control unit causes the visual field changing unit to change the imaging visual field at the speed represented by the first information in the recognized direction or change the imaging visual field by the distance represented by the first information in the recognized direction. In a fourth step, the control unit acquires at least two of the images at the timing represented by the second information from the imaging unit. In a fifth step, the control unit restores the three-dimensional shape using the images acquired from the imaging unit.

DETAILED DESCRIPTION OF THE INVENTION

Hereinafter, embodiments of the present invention will be described with reference to the drawings. Hereinafter, an example in which an image acquisition device is an endoscope device will be described. The image acquisition device may be a device having an image acquisition function and is not limited to an endoscope device.

First Embodiment

Figure 1:
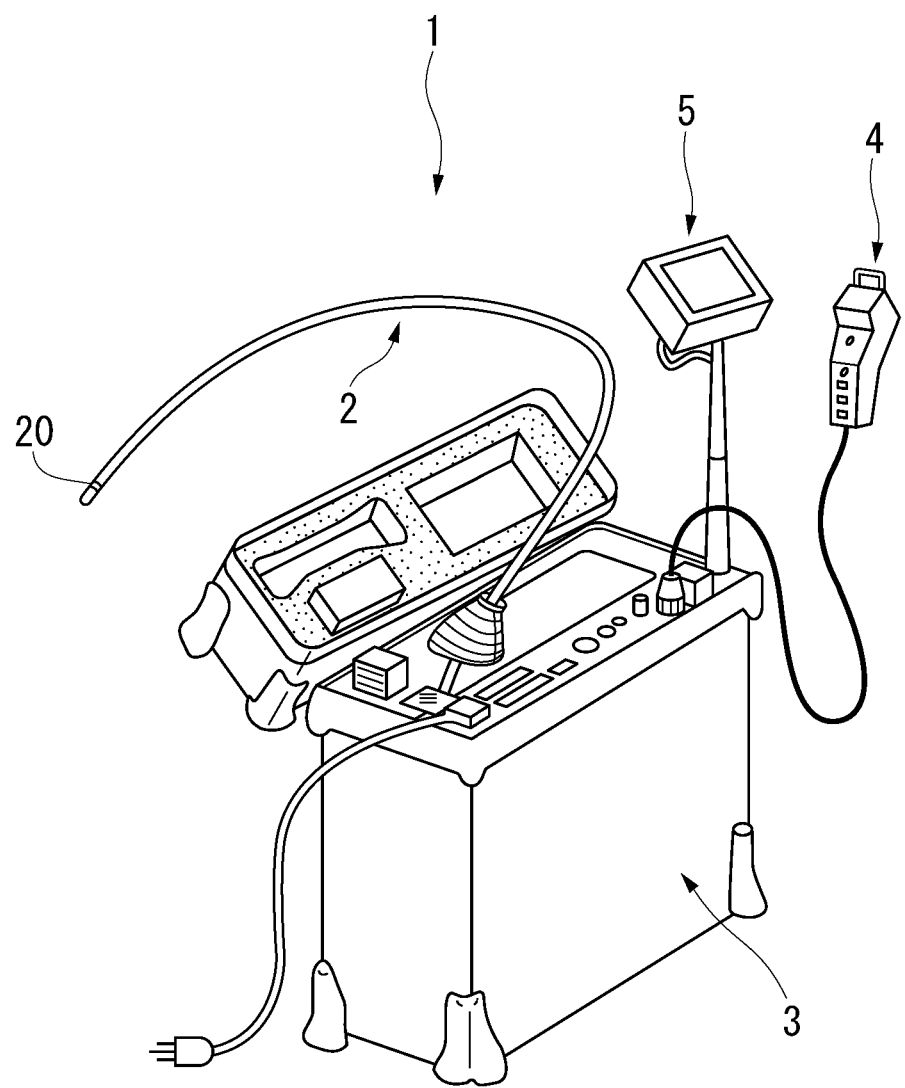
FIG. 1 is a perspective view showing the entire configuration of an endoscope device according to a first embodiment of the present invention.
Figure 2:
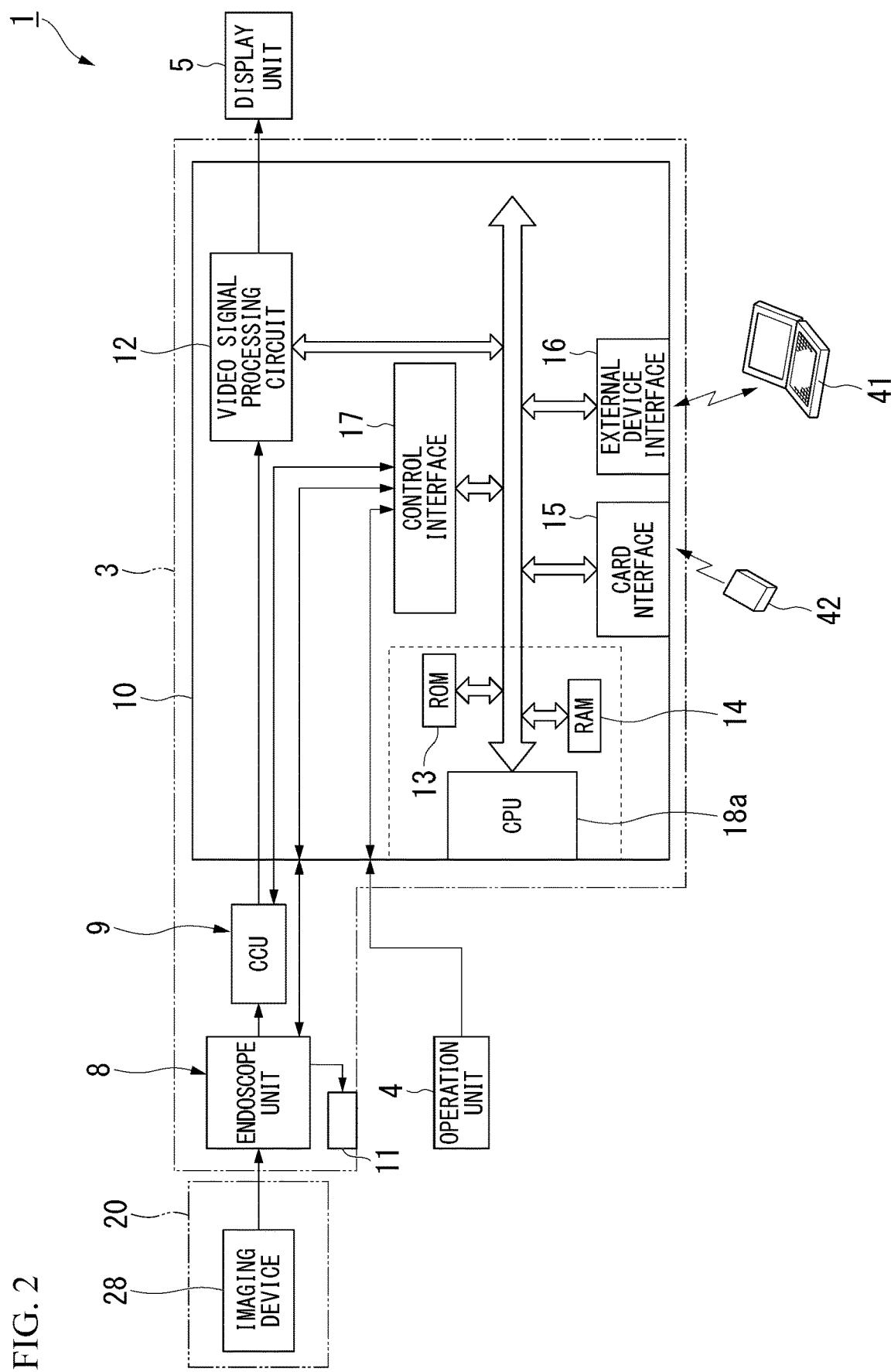
FIG. 2 is a block diagram showing the internal configuration of an endoscope device according to the first embodiment of the present invention.

FIG. 1 shows an external view of an endoscope device 1 according to a first embodiment of the present invention. FIG. 2 shows the internal configuration of the endoscope device 1. The endoscope device 1 images a subject and measures geometrical features of the subject using images. In order to observe and measure various subjects, an inspector can perform replacement of an optical adaptor mounted at a tip end of an insertion unit 2, selection of a built-in measurement processing program, and addition of a measurement processing program. Hereinafter, a case in which measurement combining three-dimensional shape restoration using structure from motion (SfM) and a user's input of a reference distance is performed will be described as one example of measurement.

The endoscope device 1 shown in FIG. 1 includes an insertion unit 2, a main body unit 3, an operation unit 4, and a display unit 5.

The insertion unit 2 is inserted into the inside of a subject. The insertion unit 2 has a long and thin bendable tube shape from the tip end 20 to a base end portion. The insertion unit 2 images a measurement part and outputs an imaging signal to the main body unit 3. An optical adapter is mounted on the tip end 20 of the insertion unit 2. For example, a monocular optical adapter is mounted on the tip end 20 of the insertion unit 2. The main body unit 3 is a control device including a housing unit that houses the insertion unit 2. The operation unit 4 accepts a user's operation for the endoscope device 1. The display unit 5 includes a display screen and displays an image of a subject acquired by the insertion unit 2, an operation menu, and the like on the display screen.

The operation unit 4 is a user interface. For example, the operation unit 4 is at least one of a button, a switch, a key, a mouse, a joystick, a touch pad, a track ball, and a touch panel. The display unit 5 is a monitor (display) such as a liquid crystal display (LCD). The display unit 5 may be a touch panel. In such a case, the operation unit 4 and the display unit 5 are integrated.

The main body unit 3 shown in FIG. 2 includes an endoscope unit 8, a camera control unit (CCU) 9, a control device 10, and a bending mechanism 11. The endoscope unit 8 includes a light source device and a bending device not shown in the drawing. The light source supplies illumination light that is necessary for observation. The bending device bends the bending mechanism 11 built into the insertion unit 2. An imaging device 28 is built into the tip end 20 of the insertion unit 2. The imaging device 28 is an image sensor. The imaging device 28 photo-electrically converts an optical image of a subject that is formed by an optical adaptor and generates an imaging signal. The CCU 9 drives the imaging device 28. An imaging signal output from the imaging device 28 is input to the CCU 9. The CCU 9 executes a pre-process including amplification, noise elimination, and the like for an imaging signal acquired by the imaging device 28. The CCU 9 converts the imaging signal for which the pre-process has been executed into a video signal such as an NTSC signal.

The control device 10 includes: a video signal processing circuit 12, a read only memory (ROM) 13, a random access memory (RAM) 14, a card interface 15, an external device interface 16, a control interface 17, and a central processing unit (CPU) 18a.

The video signal processing circuit 12 executes predetermined video processing for a video signal output from the CCU 9. For example, the video signal processing circuit 12 performs video processing related to improvement of visibility. For example, the video processing is color reproduction, gray scale correction, noise suppression, contour enhancement, and the like. The video signal processing circuit 12 also performs a process for improving measurement performance when measurement is executed. For example, the video signal processing circuit 12 combines a video signal output from the CCU 9 and a graphic image signal generated by the CPU 18a. The graphic image signal includes an image of the operation screen, measurement information, and the like. The measurement information includes an image of a cursor, an image of a designation point, measurement results, and the like. The video signal processing circuit 12 outputs a combined video signal to the display unit 5.

The ROM 13 is a nonvolatile recording medium on which a program for the CPU 18a to control the operation of the endoscope device 1 is recorded. The RAM 14 is a volatile recording medium that temporarily stores information used by the CPU 18a for controlling the endoscope device 1. The CPU 18a controls the operation of the endoscope device 1 on the basis of a program recorded in the ROM 13.

A memory card 42 that is a recording medium, which can be detached or attached, is connected to the card interface 15. The card interface 15 reads control process information, image information, and the like stored in the memory card 42 into the control device 10. In addition, the card interface 15 records control process information, image information, and the like generated by the endoscope device 1 in the memory card 42.

An external device such as a USB device is connected to the external device interface 16. For example, a personal computer 41 is connected to the external device interface 16. The external device interface 16 transmits information to the personal computer 41 and receives information from the personal computer 41. Accordingly, a monitor of the personal computer 41 can display information. In addition, by inputting an instruction to the personal computer 41, a user can perform an operation related to control of the endoscope device 1.

The control interface 17 performs communication with the operation unit 4, the endoscope unit 8, and the CCU 9 for operation control. The control interface 17 notifies an instruction input to the operation unit 4 by the user to the CPU 18a. The control interface 17 outputs control signals used for controlling the light source device and the bending device to the endoscope unit 8. The control interface 17 outputs a control signal used for controlling the imaging device 28 to the CCU 9.

A program executed by the CPU 18a may be recorded on a computer-readable recording medium. The program recorded on this recording medium may be read and executed by a computer other than the endoscope device 1. For example, the program may be read and executed by the personal computer 41. The personal computer 41 may control the endoscope device 1 by transmitting control information used for controlling the endoscope device 1 to the endoscope device 1 in accordance with a program. Alternatively, the personal computer 41 may acquire a video signal from the endoscope device 1 and perform measurement using the acquired video signal.

The program described above may be transmitted from the computer storing the program to the endoscope device 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). A combination of a program that has already been recorded in a computer and a differential program may realize the functions described above.

The endoscope device 1 described above includes an imaging device 28 (imaging unit), a bending mechanism 11 (visual field changing unit), an operation unit 4, and a CPU 18a (control unit). The imaging device 28 images a subject and generates an imaging signal. In this way, the imaging device 28 generates an image (image data) on the basis of an optical image of a subject within an imaging visual field. The image generated by the imaging device 28 is input to the CPU 18a through the video signal processing circuit 12. The bending mechanism 11 changes the imaging visual field of the imaging device 28 by bending the insertion unit 2. The visual field changing unit has only to be a mechanism that can change the imaging visual field by moving the imaging device 28 or moving a member including the imaging device 28. The operation unit 4 accepts a direction to which the imaging visual field is changed from a user.

Figure 3:
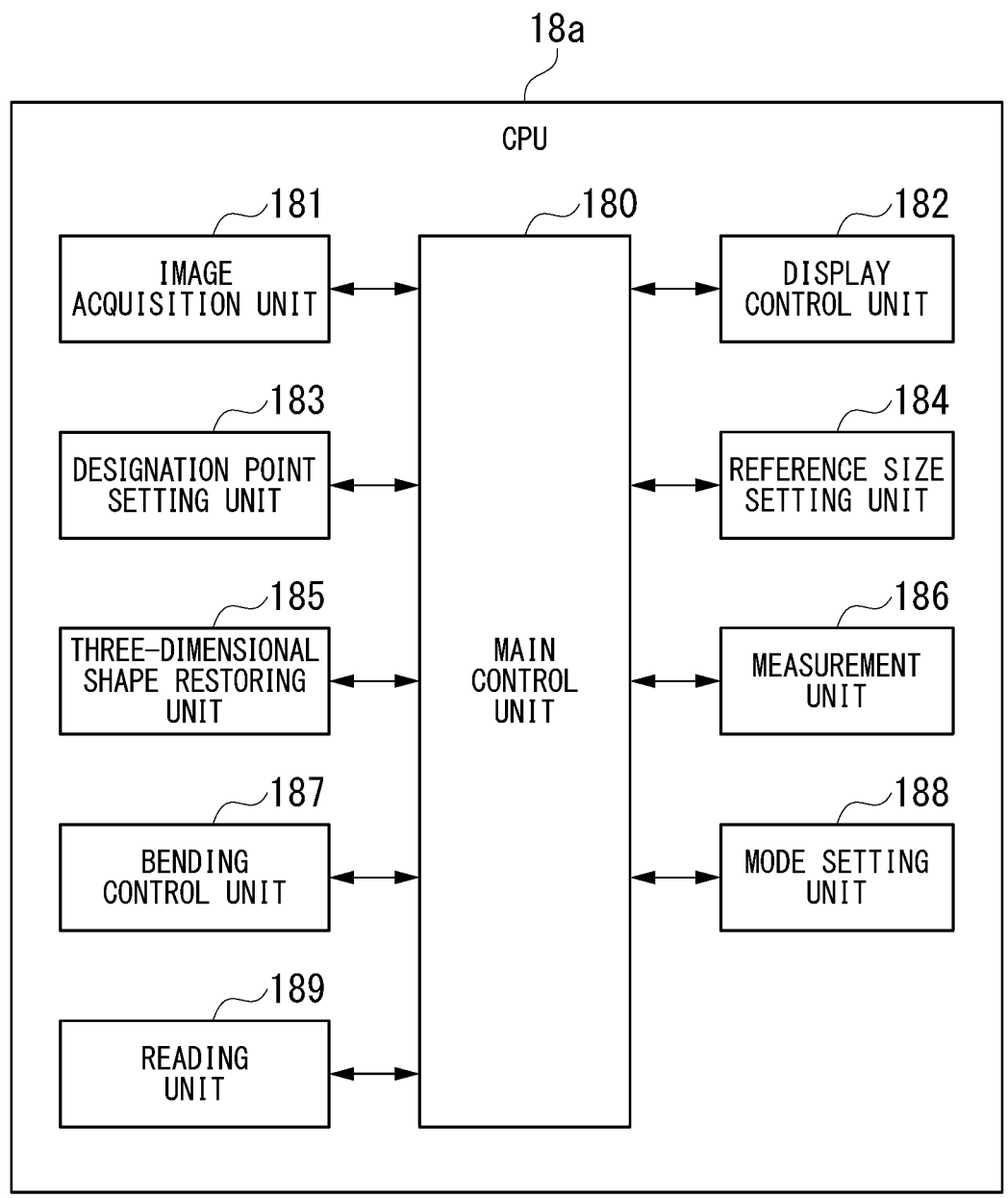
FIG. 3 is a block diagram showing the functional configuration of a CPU according to the first embodiment of the present invention.

FIG. 3 shows the functional configuration of the CPU 18a. The functions of the CPU 18a are constituted by a main control unit 180, an image acquisition unit 181, a display control unit 182, a designation point setting unit 183, a reference size setting unit 184, a three-dimensional shape restoring unit 185, a measurement unit 186, a bending control unit 187, a mode setting unit 188, and a reading unit 189. At least one of the blocks shown in FIG. 3 may be constituted by a circuit different from that of the CPU 18a.

Each unit shown in FIG. 3 may be constituted by at least one of a processor and a logic circuit. For example, the processor is at least one of a CPU, a digital signal processor (DSP), and a graphics processing unit (GPU). For example, the logic circuit is at least one of an application specific integrated circuit (ASIC) and a field-programmable gate array (FPGA). Each unit shown in FIG. 3 may include one or a plurality of processors. Each unit shown in FIG. 3 may include one or a plurality of logic circuits.

The main control unit 180 controls a process executed by each unit. The image acquisition unit 181 acquires an image generated by the imaging device 28 from the video signal processing circuit 12. The acquired image is stored in the RAM 14.

The display control unit 182 displays an image generated by the imaging device 28 on the display unit 5. For example, the display control unit 182 controls a process executed by the video signal processing circuit 12. The display control unit 182 causes the video signal processing circuit 12 to output a processed image to the display unit 5. The display unit 5 displays the image output from the video signal processing circuit 12.

The display control unit 182 displays various kinds of information on the display unit 5. In other words, the display control unit 182 displays various kinds of information on an image. Various kinds of information include a cursor, an icon, and the like. The cursor is a pointer used by a user for designating a specific position on an image. An icon is a mark that represents the position of a designation point designated on an image by a user. For example, the display control unit 182 generates a graphic image signal of various kinds of information. The display control unit 182 outputs the generated graphic image signal to the video signal processing circuit 12. The video signal processing circuit 12 composes a video signal output from the CCU 9 and a graphic image signal output from the CPU 18*a*. In this way, various kinds of information are superimposed on an image. The video signal processing circuit 12 outputs the composed video signal to the display unit 5. The display unit 5 displays the image on which various kinds of information are superimposed on the basis of the video signal.

A user inputs position information of a cursor to the operation unit 4 by operating the operation unit 4. The operation unit 4 accepts position information that is input to the operation unit 4 by a user and outputs the position information. The position information input to the operation unit 4 is input to the control interface 17 that is an input unit. The position information input to the control interface 17 is input to the CPU 18*a*. The display control unit 182 detects a position represented by the position information input to the operation unit 4. The display control unit 182 displays a cursor at the position represented by the position information input to the operation unit 4. In a case in which the display unit 5 is a touch panel, a user inputs the position information of the cursor to the operation unit 4 by touching the screen of the display unit 5.

The designation point setting unit 183 sets one or more designation points on an image. The designation point includes at least one of a measurement point representing a measurement position and a reference point representing a position of a reference size. For example, the designation point is input by a user. The designation point setting unit 183 sets one or more measurement points and one or more reference points. However, the designation point setting unit 183 may set only measurement points or reference points on an image.

A user inputs position information of measurement points and reference points to the operation unit 4 by operating the operation unit 4. The operation unit 4 accepts position information input by a user and outputs the position information. The position information input to the operation unit 4 is input to the CPU 18*a* through the control interface 17. The designation point setting unit 183 sets measurement points and reference points at positions represented by the position information on an image that is acquired by the imaging device 28 and is displayed on the display unit 5. The position information of the measurement points and the reference points set by the designation point setting unit 183 is stored in the RAM 14. The measurement points and the reference points are set by associating the measurement points and the reference points with a specific image.

A designation point is coordinate information of a target position in an image determined on the basis of a user's instruction. As described above, designation points include measurement points and reference points. It is assumed that designation points are points used for designating a measurement position and a reference size. A means for determining a designation point is not limited to a user's input. For example, the designation point setting unit 183 may automatically determine designation points on the basis of information registered in the endoscope device 1 in advance. For example, a reference image in which designation points are set in advance may be taken in by the endoscope device 1 from the personal computer 41 or the memory card 42. The designation point setting unit 183 may detect points similar to designation points set on a reference image from an image through pattern matching and set the detected points as designation points in the image.

Designation of measurement points or reference points means that a user instructs the endoscope device 1 of the measurement points or the reference points. A user designates a measurement point or a reference point by designating a position on an image using the cursor. Alternatively, a user may designate a measurement point or a reference point by touching the screen of the display unit 5. The setting of a measurement point means that the designation point setting unit 183 associates the measurement point with an image. The setting of a reference point means that the designation point setting unit 183 associates a reference point with an image.

The shapes and sizes of the cursor and the icon are not limited as long as a designation point can be notified to the user. In addition, although a term "point" is used for the convenience of description, a designation point does not need to be one point corresponding to one pixel on the screen. A designation point may include a region having an arbitrary size. A designation point may include a region that can be designated in units of sub-pixels.

A user inputs a reference size to the operation unit 4 by operating the operation unit 4. The operation unit 4 accepts the reference size input to the operation unit 4 by the user and outputs the reference size. The reference size input to the operation unit 4 is input to the CPU 18*a* through the control interface 17. When the reference size is input to the operation unit 4, the reference size setting unit 184 sets the reference size to an image that is acquired by the imaging device 28 and is displayed on the display unit 5. The reference size set by the reference size setting unit 184 is stored in the RAM 14. A reference size is set by associating the reference size with a specific image. The designation of a reference size means that a user instructs the endoscope device 1 of the reference size. The setting of a reference size means that the reference size setting unit 184 associates the reference size with an image.

In the following example, a reference size is a reference distance between two points. As described above, the reference distance is given by a user. For example, a user may designate two reference points and designate a distance therebetween as a reference distance. A reference distance designated by a user may be known. For example, a reference distance in a known structure of a subject image may be designated by a user.

The reference distance may be input from a distance acquisition unit not shown in the drawing to the endoscope device 1. For example, the distance acquisition unit may include an active projection system and a three-dimensional measurement unit. The active projection system projects light having the form of a point, a line, stripes, or the like on a subject. The three-dimensional measurement unit calculates a reference distance on the basis of an image of the subject on which the light is projected. The three-dimensional measurement unit may acquire a reference point on the basis of a position at which a reference distance is calculated. A reference point representing the position of a reference size may be input from a device that measures the reference size. For example, a reference point may be input from the three-dimensional measurement unit or the distance acquisition unit to the endoscope device 1. The distance acquisition unit may calculate a reference distance using a flight time measuring method (time of flight). The distance acquisition unit may be a sensing unit that uses a sensor such as a three-dimensional acceleration sensor, a gyro sensor, or a radiowave sensor.

For example, the external device interface 16 may acquire a reference point and a reference distance from the distance acquisition unit. As described above, in one example, the distance acquisition unit includes an active projection system and a three-dimensional measurement unit. A reference point and a reference distance output from the distance acquisition unit are input to the external device interface 16. The reference point and the reference distance input to the external device interface 16 are input to the CPU 18a. The designation point setting unit 183 sets the reference point output from the distance acquisition unit in an image. The reference size setting unit 184 sets the reference distance output from the distance acquisition unit in the image. In this case, since the reference point and the reference distance are automatically determined, the time of a user is not required.

The endoscope device 1 may include a memory that stores a reference size calculated in advance. The reference size setting unit 184 may read a reference size for the reference point set by the designation point setting unit 183 from a memory and may set the read reference size in the image.

The three-dimensional shape restoring unit 185 restores a three-dimensional shape of a subject, in other words, a measurement target using a plurality of images acquired by the image acquisition unit 181. When a plurality of images are generated, at least imaging positions or imaging postures or both thereof are different from each other. Accordingly, when a plurality of images are generated, the imaging visual fields of the imaging device 28 are different from each other. A method of restoring a three-dimensional shape will be described later.

The measurement unit 186 measures an object that is a measurement target on the basis of a three-dimensional shape, a plurality of designation points, and a reference size. The three-dimensional shape is restored by the three-dimensional shape restoring unit 185. The plurality of designation points are measurement points and reference points. The plurality of designation points are set by the designation point setting unit 183. The reference size is set by the reference size setting unit 184. The measurement unit 186 calculates three-dimensional coordinates corresponding to measurement points using two-dimensional coordinates of the measurement points and the reference point and the reference distance. The measurement unit 186 measures a three-dimensional size of the subject on the basis of the three-dimensional coordinates corresponding to the measurement points.

The bending control unit 187 controls the bending mechanism 11 used for bending the tip end 20 of the insertion unit 2. For example, the bending control unit 187 generates a command used for bending the tip end 20 of the insertion unit 2 in one direction on the basis of an instruction from the main control unit 180. The command generated by the bending control unit 187 is output to the endoscope unit 8 through the control interface 17. The endoscope unit 8 bends the tip end 20 of the insertion unit 2 by driving the bending mechanism 11 on the basis of the command.

A user inputs a direction in which a bending angle of the tip end 20 of the insertion unit 2 is changed to the operation unit 4 by operating the operation unit 4. In other words, the user inputs a direction in which the imaging visual field is changed to the operation unit 4. Hereinafter, a direction in which the bending angle of the tip end 20 of the insertion unit 2 is changed will be referred to as an angle change direction. The operation unit 4 accepts the angle change direction input to the operation unit 4 by the user and outputs the angle change direction. The angle change direction input to the operation unit 4 is input to the CPU 18a through the control interface 17. The bending control unit 187 generates a command used for driving the bending mechanism 11 on the basis of the angle change direction input to the operation unit 4.

The mode setting unit 188 sets a predetermined operation mode to the endoscope device 1. For example, the mode setting unit 188 sets one of an image acquisition mode and an inspection mode (image display mode) to the endoscope device 1. The image acquisition mode is a mode that is used for acquiring images used for restoring a three-dimensional shape of a subject. The inspection mode is a mode that is used for displaying images generated at intervals based on an imaging frame rate by the imaging device 28 on the display unit 5.

A user inputs an instruction for an operation mode to the operation unit 4 by operating the operation unit 4. The operation unit 4 accepts an instruction input to the operation unit 4 by the user and outputs the instruction. The instruction input to the operation unit 4 is input to the CPU 18a through the control interface 17. The mode setting unit 188 determines an operation mode instructed by the user on the basis of the instruction input to the operation unit 4. The mode setting unit 188 sets the operation mode instructed by the user to the endoscope device 1. The mode setting unit 188 switches the operation mode set in the endoscope device 1 between the image acquisition mode and the inspection mode on the basis of the instruction input to the operation unit 4.

In a case in which the image acquisition mode is set in the endoscope device 1, the reading unit 189 reads image acquisition condition information defining image acquisition conditions from a storage medium. In a case in which the inspection mode is set in the endoscope device 1, the reading unit 189 reads image display condition information defining image display conditions from a storage medium. The image acquisition condition information and the image display condition information include imaging visual field change information and timing information. The imaging visual field change information represents a speed at which the imaging visual field is changed or a distance by which the imaging visual field is changed. The timing information represents a timing at which an image used in the image acquisition mode or the inspection mode is acquired from the imaging device 28. For example, the timing information in the image acquisition mode represents a timing based on a speed at which the imaging visual field is changed or a distance by which the imaging visual field is changed. The timing information in the inspection mode represents a timing that is the same as an imaging timing of the imaging device 28.

The reading unit 189 reads the image acquisition condition information and the image display condition information from the RAM 14. For example, the memory card 42 stores the image acquisition condition information and the image display condition information. The image acquisition condition information and the image display condition information are transmitted from the memory card 42 to the RAM 14 through the card interface 15. The personal computer 41 may store the image acquisition condition information and the image display condition information. The image acquisition condition information and the image display condition information may be transmitted from the personal computer 41 to the RAM 14 through the external device interface 16. A server on a network (a cloud server or the like) may store the image acquisition condition information and the image display condition information. The image acquisition condition information and the image display condition information may be transmitted from a server to the RAM 14 through the external device interface 16.

A schematic operation of the endoscope device 1 in the image acquisition mode will be described. The operation unit 4 accepts a direction in which the imaging visual field is changed from a user. In a case in which the image acquisition mode is set to the endoscope device 1, the bending control unit 187 recognizes a direction accepted by the operation unit 4. The reading unit 189 reads first information and second information that define the image acquisition conditions in the image acquisition mode from the RAM 14. The first information represents a speed at which the imaging visual field is changed or a distance by which the imaging visual field is changed. The second information represents a timing at which images used for restoring the three-dimensional shape are acquired. The bending control unit 187 causes the bending mechanism 11 to change the imaging visual field at a speed represented by the first information in a recognized direction or to change the imaging visual field by a distance represented by the first information in a recognized direction. The image acquisition unit 181 acquires at least two images at timings represented by the second information from the imaging device 28. The three-dimensional shape restoring unit 185 restores the three-dimensional shape of the subject using at least two images acquired from the imaging device 28. The bending mechanism 11 changes the imaging visual field at a speed represented by the first information in the recognized direction or changes the imaging visual field by a distance represented by the first information in the recognized direction.

A schematic operation of the endoscope device 1 in the inspection mode will be described. The operation unit 4 accepts a direction in which the imaging visual field is changed from a user. In a case in which the inspection mode is set to the endoscope device 1, the bending control unit 187 recognizes a direction accepted by the operation unit 4. The reading unit 189 reads third information and fourth information that define display conditions in the inspection mode from the RAM 14. The third information represents a speed at which the imaging visual field is changed or a distance by which the imaging visual field is changed. The fourth information represents a timing at which an image used for displaying an image is acquired. The bending control unit 187 causes the bending mechanism 11 to change the imaging visual field at a speed represented by the third information in the recognized direction or to change the imaging visual field by a distance represented by the third information in the recognized direction. The display control unit 182 outputs an image output from the imaging device 28 at a timing represented by the fourth information to the display unit 5. The bending mechanism 11 changes the imaging visual field at a speed represented by the third information in a recognized direction or changes an imaging visual field by a distance represented by the third information in the recognized direction.

The sequence of specific processes executed by the three-dimensional shape restoring unit 185 and the measurement unit 186 will be described. The three-dimensional shape restoring unit 185 receives a plurality of images output from the video signal processing circuit 12 and coordinate information of designation points stored in the RAM 14. Hereinafter, an example in which the three-dimensional shape restoring unit 185 receives two images from the video signal processing circuit 12 will be described. Also in a case in which three or more images are used, a basic principle is not changed from that of the case in which two images are used. A method described below may be applied also to a case in which three or more images are used.

Figure 4:
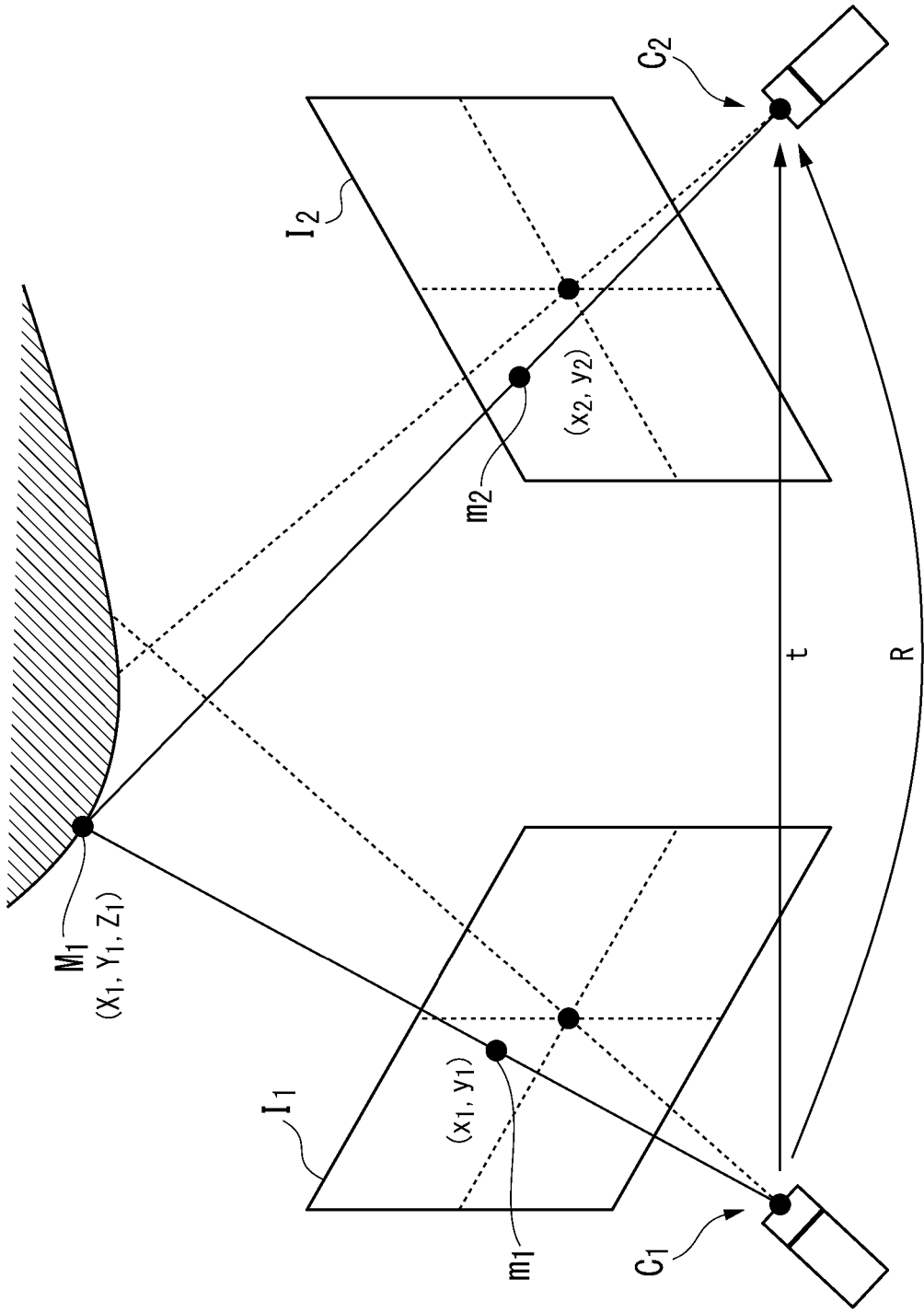
FIG. 4 is a schematic view showing a status of image acquisition according to the first embodiment of the present invention.

FIG. 4 schematically shows a status of image acquisition in a case in which two images of a subject that is a measurement target are acquired. In the following description, a term "camera" in a broad sense will be used. A camera in the following description, specifically, represents an observation optical system of an endoscope tip end (the tip end 20 of the insertion unit 2).

As shown in FIG. 4, first, an image $I_1$ is acquired in an imaging state $c_1$ of the camera. Next, an image $I_2$ is acquired in an imaging state $c_2$ of the camera. At least one of an imaging position and an imaging posture is different between the imaging state $c_1$ and the imaging state $c_2$. In the case shown in FIG. 4, both the imaging position and the imaging posture are different between the imaging state $c_1$ and the imaging state $c_2$.

In each embodiment of the present invention, it is assumed that the image $I_1$ and the image $I_2$ are acquired by the same endoscope. In addition, in each embodiment of the present invention, it is assumed that parameters of an objective optical system of the endoscope do not change. The parameters of the objective optical system are a focal distance, a distortion aberration, a pixel size of an image sensor, and the like. Hereinafter, for the convenience of description, the parameters of the objective optical system will be abbreviated to internal parameters. When such conditions are assumed, the internal parameters describing characteristics of the optical system of the endoscope can be commonly used regardless of the position and the posture of the camera disposed at the endoscope tip end. In each embodiment of the present invention, it is assumed that the internal parameters are acquired at the time of factory shipment, and the internal parameters are known at the time of measurement.

In a case in which the image $I_1$ and the image $I_2$ are acquired using different endoscope devices, common internal parameters cannot be used. In addition, in a case in which the internal parameters are different for each image although the image $I_1$ and the image $I_2$ are acquired using the same endoscope device, common internal parameters cannot be used. However, calculation can be performed using the internal parameters as unknown quantities. For this reason, the subsequent process does not greatly change in accordance with whether or not the internal parameters are known. In the former case, endoscope devices may store individual internal parameters in advance.

Figure 5:
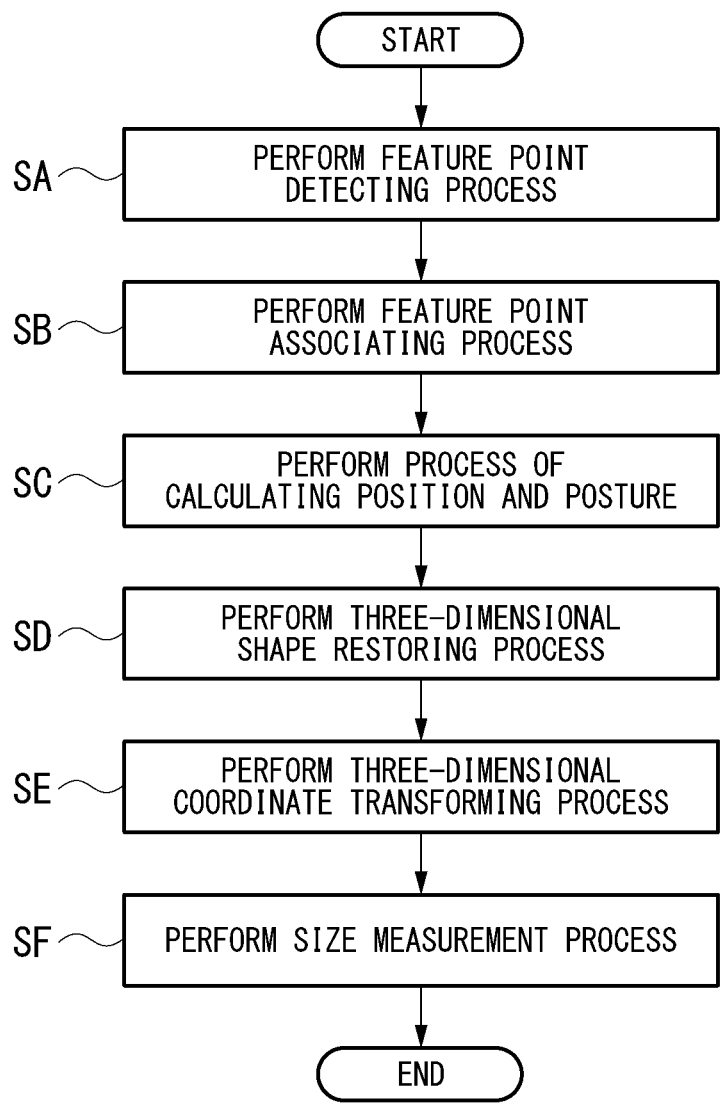
FIG. 5 is a flowchart showing the sequence of a process for three-dimensional shape restoration and measurement according to the first embodiment of the present invention.

A sequence for calculating three-dimensional coordinates of a subject on the basis of acquired subject images will be described with reference to FIG. 5. FIG. 5 shows the sequence of a process for three-dimensional shape restoration and measurement.

First, the three-dimensional shape restoring unit 185 executes a feature point detecting process (Step SA). The three-dimensional shape restoring unit 185 detects a feature point of acquired two images in the feature point detecting process. Here, a feature point represents a corner, an edge, and the like in which an image luminance gradient is large in subject information represented in the image. As a method of detecting this feature point, a scale-invariant feature transform (SIFT), a feature from accelerated segment test (FAST), or the like is used. By using such a method, a feature point inside an image can be detected.

FIG. 4 shows an example in which a feature point $m_1$ is detected from the image $I_1$, and a feature point $m_2$ is detected from the image $I_2$. Although only one feature point of each image is displayed in FIG. 4, actually, a plurality of feature points are detected for each image. There is a possibility that the number of feature points detected in each image is different. Each feature point detected from each image is converted into data called a feature quantity. The feature quantity is data that represents a feature of a feature point.

After Step SA, the three-dimensional shape restoring unit 185 executes a feature point associating process (Step SB). In the association point associating process, the three-dimensional shape restoring unit 185 compares correlations of feature quantities between images for each feature point detected by a feature point detecting process in Step SA. As a result of the comparison of the correlations of the feature quantities, in a case in which feature points of which feature quantities are close are found in each image, the three-dimensional shape restoring unit 185 stores the information in the RAM 14. On the other hand, in a case in which feature points of which feature quantities are close are not found, the three-dimensional shape restoring unit 185 discards information of the feature points.

After Step SB, the three-dimensional shape restoring unit 185 reads coordinates of feature points of two images associated with each other (a feature point pair) from the RAM 14. The three-dimensional shape restoring unit 185 executes a process of calculating a position and a posture on the basis of the read coordinates (Step SC). In the process of calculating a position and a posture, the three-dimensional shape restoring unit 185 calculates a relative position and a relative posture between an imaging state $c_1$ of a camera that has acquired the image $I_1$ and an imaging state $c_2$ of the camera that has acquired the image $I_2$. More specifically, the three-dimensional shape restoring unit 185 calculates a matrix E by solving the following Equation (1) using an epipolar restriction.

$$p_1^T E p_2 = 0 \quad E = [t]_X R \because [t]_X = \begin{pmatrix} 0 & -t_z & t_y \\ t_z & 0 & -t_x \\ -t_y & t_x & 0 \end{pmatrix} \quad (1)$$

The matrix E is called a basic matrix. The basic matrix E is a matrix storing a relative position and a relative posture between the imaging state $c_1$ of the camera that has acquired the image $I_1$ and the imaging state $c_2$ of the camera that has acquired the image $I_2$. In Equation (1), $p_1$ is a matrix including coordinates of a feature point detected from the image $I_1$. In addition, $p_2$ is a matrix including coordinates of a feature point detected from the image $I_2$. The basic matrix E includes information related to a relative position and a relative posture of the camera and thus corresponds to external parameters of the camera. The basic matrix E can be solved using a known algorithm.

As shown in FIG. 4, Equation (2) and Equation (3) are satisfied in a case in which the amount of position change of the camera is t, and the amount of posture change of the camera is R.

$$t = (t_x, t_y, t_z) \quad (2)$$

$$R = R_x(\alpha) R_y(\beta) R_z(\gamma) \quad (3)$$
$$= \begin{pmatrix} 1 & 0 & 0 \\ 0 & \cos\alpha & -\sin\alpha \\ 0 & \sin\alpha & \cos\alpha \end{pmatrix} \begin{pmatrix} \cos\beta & 0 & \sin\beta \\ 0 & 1 & 0 \\ -\sin\beta & 0 & \cos\beta \end{pmatrix} \begin{pmatrix} \cos\gamma & -\sin\gamma & 0 \\ \sin\gamma & \cos\gamma & 0 \\ 0 & 0 & 1 \end{pmatrix}$$

In Equation (2), $t_x$ is the amount of movement in an x-axis direction, $t_y$ is the amount of movement in a y-axis direction, and $t_z$ is the amount of movement in a z-axis direction. In Equation (3), $R_x(\alpha)$ is a rotation amount $\alpha$ around the x-axis, $R_y(\beta)$ is a rotation amount $\beta$ around the y axis, and $R_z(\gamma)$ is a rotation amount $\gamma$ around the z axis. After the basic matrix E is calculated, in order to improve restoration accuracy of three-dimensional coordinates, an optimization process called bundle adjustment may be executed. Generally, a process called an SfM includes processes of Step SA, Step SB, and Step SC executed after an image is acquired.

After Step SC, the three-dimensional shape restoring unit 185 executes a process of restoring a three-dimensional shape of a subject on the basis of a relative position and a relative posture of the camera (the amount of position change t and the amount of posture change R) calculated in Step SC (Step SD). As a technique for restoring the three-dimensional shape of the subject, there is a matching process using patch-based multi-view stereo (PMVS) and parallelization stereo and the like. However, a means therefor is not particularly limited.

After Step SD, the measurement unit 186 executes a three-dimensional coordinate transforming process on the basis of the three-dimensional shape data γ calculated in the three-dimensional shape restoring process in Step SD and the information of the reference distance read from the RAM 14. The measurement unit 186 transforms the three-dimensional shape data of a subject into three-dimensional coordinate data having a dimension of a length in the three-dimensional coordinate transforming process (Step SE).

After Step SE, the measurement unit 186 executes a size measurement process on the basis of the three-dimensional coordinate data of the subject (Step SF). The size measurement process has no difference from a measurement process implemented in a conventional industrial endoscope, and thus, detailed description thereof is omitted. For example, the measurement unit 186 performs size measurement such as distance between two points measurement, face reference measurement, and the like in accordance with a measurement mode selected by a user.

Figure 6:
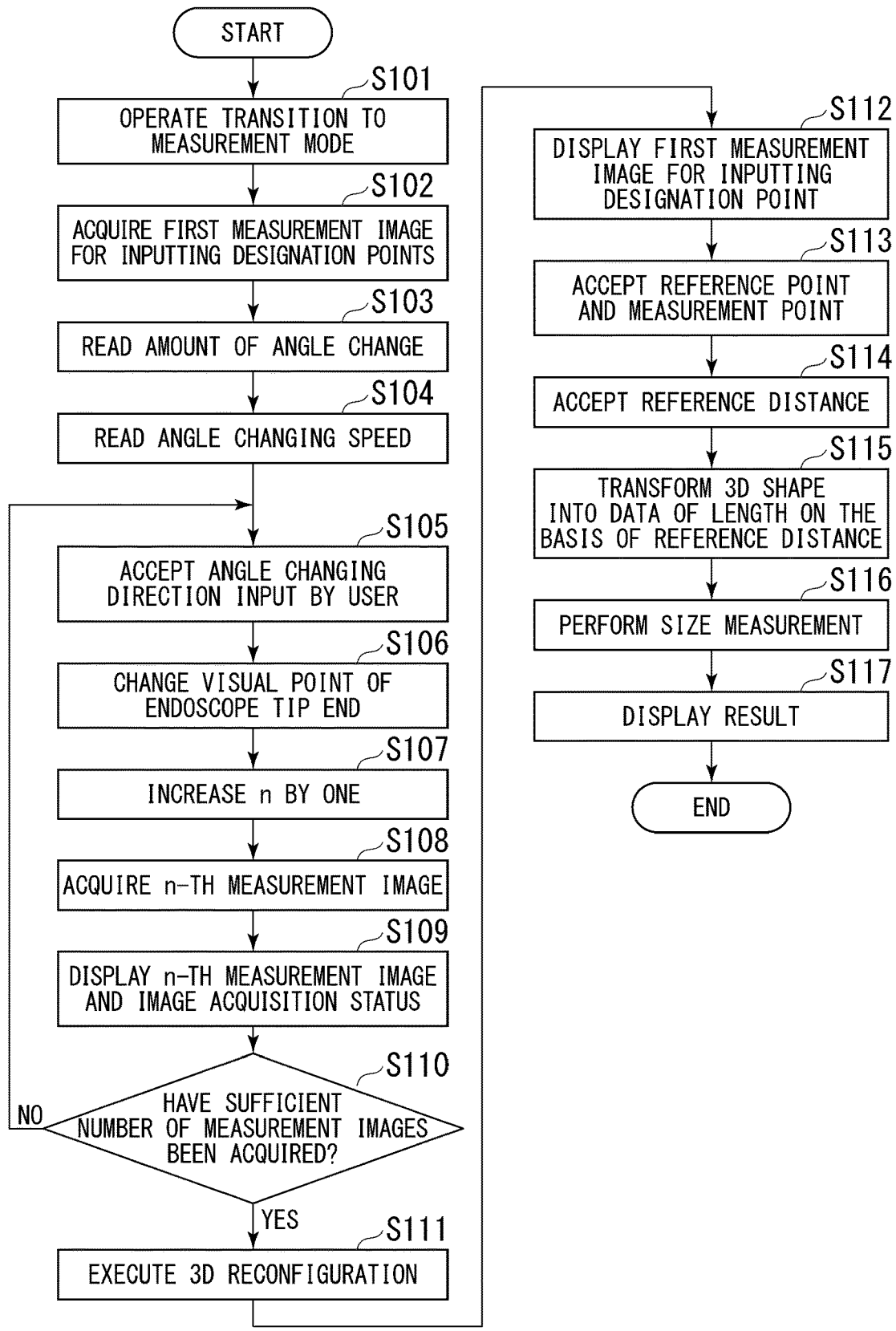
FIG. 6 is a flowchart showing the sequence of a measurement process according to the first embodiment of the present invention.

The entire measurement process according to the first embodiment will be described with reference to FIG. 6. FIG. 6 shows a sequence of a measurement process.

In an inspection using an endoscope, a user inspects whether or not there is a defect or damage by checking the status of the subject in a live image. A mode of the endoscope device 1 at this time is called an inspection mode. During an inspection, in a case in which a defect or damage that is a measurement target is found in the subject or the like, a user requests execution of measurement. At this time, in order to cause the operation mode of the endoscope device 1 to transition to the measurement mode, the user operates the operation unit 4 (Step S101). For example, when a user taps an icon, which represents a transition to the measurement mode, displayed on the display unit 5, the operation mode of the endoscope device 1 transitions from the inspection mode to the measurement mode. Alternatively, the user may press a measurement mode transition button using an input device such as a remote controller. An operation used for causing the operation mode of the endoscope device 1 to transitions from the inspection mode to the measurement mode is not limited to that of the example described above. The measurement mode is a mode in which a combination of functions defined in the image acquisition mode described above and the measurement function is executed.

After Step S101, a first measurement image used for inputting designation points is acquired. In other words, the imaging device 28 generates a first measurement image by imaging a subject once. The image acquisition unit 181 acquires the first measurement image generated by the imaging device 28 (Step S102). Second information included in the image acquisition condition information represents that a measurement image is acquired at a timing at which the operation mode of the endoscope device 1 transitions from the inspection mode to the measurement mode.

After Step S102, the reading unit 189 reads the amount of angle change from the RAM 14 (Step S103). The amount of angle change represents the amount of change in the bending angle of the tip end 20 of the insertion unit 2. The amount of angle change corresponds to the first information included in the image acquisition condition information. The amount of angle change corresponds to the distance by which the imaging visual field is changed. The amount of angle change is the amount of change in the bending angle between two imaging timings.

After Step S103, the reading unit 189 reads an angle changing speed from the RAM 14 (Step S104). The angle changing speed represents a speed at which the bending angle of the tip end 20 of the insertion unit 2 is changed. The angle changing speed corresponds to the first information included in the image acquisition condition information. The angle changing speed corresponds to a speed at which the imaging visual field is changed. The angle changing speed is a changing speed of the bending angle between two imaging timings.

The amount of angle change is set to the amount of overlapping between imaging visual fields in imaging performed twice. In other words, the amount of angle change is set to the amount of overlapping between regions of two measurement images acquired in imaging performed twice. In this way, the reliability of a result of the SfM process is improved. The angle changing speed is set to a speed at which there is no influence of motion blur on a measurement image. Accordingly, the efficiency of acquisition of a measurement image is improved.

In an embodiment of the present invention, both the angle changing amount and the angle changing speed are read from the RAM 14. Each aspect of the present invention is not limited to this method. For example, the amount of movement of the endoscope tip end is estimated on the basis of a plurality of images that are sequentially acquired, and the amount of angle change of the endoscope tip end may be adaptively controlled in accordance with the estimated amount. Alternatively, a user may be allowed to be able to designate an angle changing speed by operating the operation unit 4.

A user, in order to acquire a measurement image of a region recognized as a measurement target by the user, inputs an angle changing direction to the operation unit 4. After Step S104, the operation unit 4 accepts the angle changing direction from the user. The angle changing direction input to the operation unit 4 is input to the CPU 18a through the control interface 17. The bending control unit 187 recognizes the angle changing direction input to the operation unit 4 (Step S105). The user may input the angle changing direction by operating an input device such as a touch panel.

After Step S105, the bending control unit 187 generates a command used for bending the endoscope tip end in the angle changing direction received from the user. This command defines an operation of changing a bending angle by the amount corresponding to the amount of angle change at a speed corresponding to the angle changing speed. The bending control unit 187 drives the bending mechanism 11 by outputting the generated command to the endoscope unit 8 and bends the endoscope tip end. In this way, a visual point of the endoscope tip end is changed (Step S106).

In an embodiment of the present invention, it is assumed that the endoscope tip end is stationary after the endoscope tip end moves by a predetermined amount of angle change. Accordingly, an image having no motion blur can be acquired. A time in which the endoscope tip end is stationary has only to be a time required for acquisition of at least one image. For example, this time is approximately the same as a reciprocal of a frame rate. In a case in which the movement of the endoscope tip end occurs within a time that is assumed to be sufficiently smaller than an exposure time of the camera, the endoscope tip end does not need to be stationary. In other words slow movement of a degree at which the endoscope tip end may be regarded to be stationary can be allowed.

After Step S106, a variable n increases by one (Step S107). After Step S107, the image acquisition unit 181 acquires an n-th measurement image generated by the imaging device 28 (Step S108). The variable n represents the number of measurement images acquired for restoration and measurement of the three-dimensional shape. When the process of Step S101 is executed, the variable n is "2." When the process of Step S108 is executed for the first time, the image acquisition unit 181 acquires a second measurement image.

In Step S108, the image acquisition unit 181 acquires an n-th measurement image at a timing represented by the second information included in the image acquisition condition information. For example, the second information represents that a measurement image is acquired at a timing at which a bending angle is changed for a predetermined time at the angle changing speed. Alternatively, the second information represents that a measurement image is acquired at a timing at which the bending angle is changed by the amount of angle change.

While a visual point of the endoscope tip end changes in Step S106, the imaging device 28 executes imaging at intervals based on the imaging frame rate. A measurement image acquired in Step S108 is an image that is generated by the imaging device 28 when the change of the visual point of the endoscope tip end ends. While the visual point of the endoscope tip end changes in Step S106, the imaging device 28 may stop imaging. After a predetermined time elapses from the timing at which the change of the visual point of the endoscope tip end ends, the imaging device 28 may execute imaging, and an n-th measurement image may be acquired generated by the imaging device 28.

The image acquisition process performed for the first time includes the processes of Steps S105, S106, S107, and S108. When the image acquisition process is executed for the first time, one measurement image is acquired.

After Step S108, the display control unit 182 displays the acquired n-th measurement image on the display unit 5. In addition, the display control unit 182 displays information representing a progress status related to the acquisition of a measurement image on the display unit 5 (Step S109).

Figure 7:
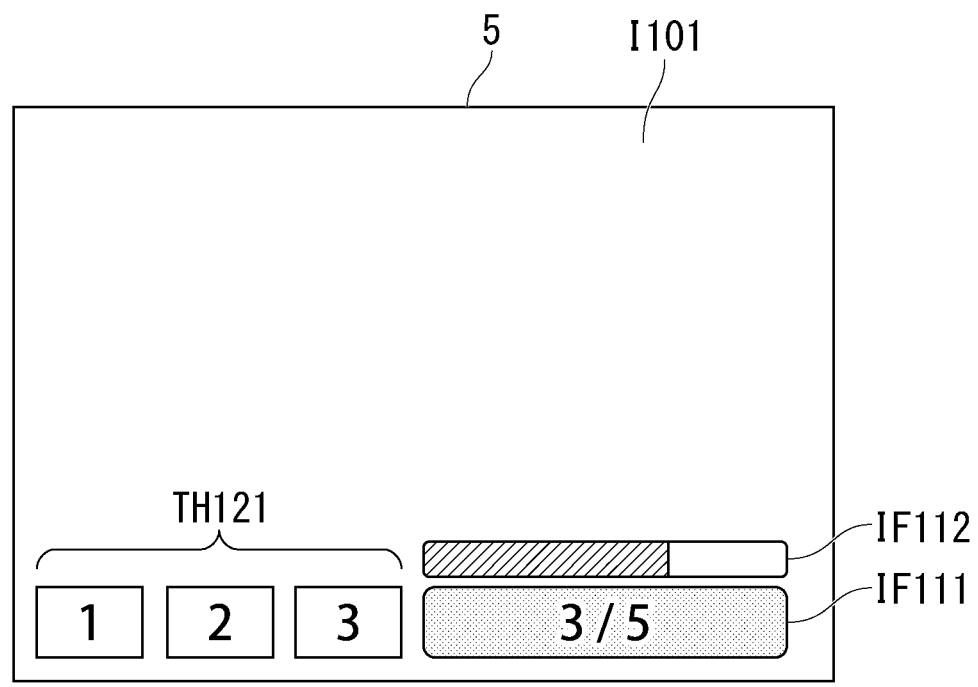
FIG. 7 is a diagram showing an image displayed on a display unit according to the first embodiment of the present invention.

The process of Step S109 will be described with reference to FIG. 7. FIG. 7 shows an image that is displayed on the display unit 5. The minimum number of measurement images required for SfM is set in the endoscope device 1 in advance. For example, the number of images can be experimentally acquired on the basis of a result of SfM that have previously been executed. The number of images is two or more. Hereinafter, although an example, in which the number of images is five will be described, the number of images is not limited to five. Hereinafter, a process executed in Step S109 when three measurement images are acquired will be described.

First, the display control unit 182 displays an n-th measurement image I101 on the display unit 5. After the n-th measurement image I101 is displayed, the display control unit 182 displays information representing a progress status on the n-th measurement image I101. For example, the display control unit 182 generates a graphic image signal of information representing the progress status. Thereafter, a process similar to the process for displaying the cursor is executed. The display unit 5 displays an n-th measurement image I101 on which the information representing the progress status is superimposed.

In the example shown in FIG. 7, information IF111 and information IF112 are displayed. The information IF111 represents a minimum number of measurement images required for SfM and the number of measurement images that have been acquired until now. The information IF111 includes two numbers. A number on the right side in the information IF111 represents the minimum number of measurement images required for SfM. A number on the left side in the information IF111 represents the number of measurement images that have been acquired until now. The information IF112 represents a progress status as a progress bar. In addition, in the example shown in FIG. 7, three thumbnail images TH121 are displayed. Each thumbnail image TH121 is a reduced image generated by decreasing the number of pixels of a measurement image.

The endoscope device 1 has only to be configured to be able to notify, to a user, the number of images to be acquired from now or a degree of a remaining time to be taken until the process of acquiring measurement images can be completed. When the number of acquired measurement images reaches the minimum number of measurement images required for SfM, the endoscope device 1 can end the process for acquiring measurement images. Any display method may be used as long as the progress status of acquisition of measurement images can be notified to the user.

The display control unit 182 displays at least one of measurement images acquired from the imaging device 28 on the display unit 5 in Step S109. In a case in which two or more measurement images have already been acquired, two or more measurement images may be displayed in Step S109. In Step S109, the display control unit 182 counts a first number and displays information representing a ratio of the first number to a second number on the display unit 5. The first number represents the number of measurement images acquired from the imaging device 28. In other words, in the example described above, the first number represents the number of measurement images that have been acquired until now. The second number represents the number of measurement images required for restoration of a three-dimensional shape and is at least two. In other words, in the example described above, the second number represents the minimum number of measurement images required for SfM. In the example described above, the information representing the ratio described above is the information IF111 and the information IF112.

In Step S109, the display control unit 182 generates a thumbnail image by decreasing the number of pixels of the image acquired from the imaging device 28. In Step S109, the display control unit 182 displays the thumbnail image on the display unit 5. In a case in which two or more measurement images have already been acquired, two or more thumbnail images may be generated and displayed in Step S109. In the example described above, three thumbnail images TH121 are displayed on the display unit 5.

After Step S109, the main control unit 180 compares a variable n with a predetermined number of images. The variable n represents the number of acquired measurement images. The predetermined number of images represents the minimum number of measurement images required for SfM. The predetermined number of images is at least two. The main control unit 180 determines whether or not the number of acquired measurement images has reached the predetermined number of images on the basis of a result of the comparison (Step S110).

After the acquisition of measurement images based on the image acquisition condition ends, the main control unit 180 compares a first number with a second number in Step S110. The first number represents the number of measurement images acquired from the imaging device 28. The second number represents the number of measurement images required for restoration of a three-dimensional shape and is at least two.

In a case in which the main control unit 180 determines that the number of acquired measurement images has reached the predetermined number in Step S110, the three-dimensional shape restoring unit 185 executes 3D reconfiguration using the predetermined number of measurement images acquired by the image acquisition unit 181 (Step S111). The execution of 3D reconfiguration includes both SfM and a process of restoring a dense three-dimensional shape of a subject. In the 3D reconfiguration, a predetermined number of measurement images are used. In a case in which the main control unit 180 determines that the number of acquired measurement images has not reached the predetermined number in Step S110, the process of Step S105 is executed. Thereafter, the image acquisition process is executed again, and a measurement image is acquired. The image acquisition process is repeated until the predetermined number of measurement images are acquired.

The flow of image acquisition until the number of acquired measurement images reaches the predetermined number will be described with reference to FIGS. 8 and 9. An example in which the minimum number of measurement images required for SfM is five will be described.

In Step S102, a first measurement image I201 is acquired. After the first measurement image I201 is acquired, the operation unit 4 accepts an angle changing direction D211 from a user in Step S105. In Step S106 of the image acquisition process of the first time, the bending angle is changed in accordance with the angle changing direction D211. After the change of the bending angle ends, a second measurement image I202 is acquired in Step S108 of the image acquisition process of the first time. After the second measurement image I202 is acquired, the operation unit 4 accepts an angle changing direction D212 from a user in Step S105. In Step S106 of the image acquisition process of the second time, the bending angle is changed in accordance with the angle changing direction D212. After the change of the bending angle ends, a third measurement image I203 is acquired in Step S108 of the image acquisition process of the second time.

After the third measurement image I203 is acquired, the operation unit 4 accepts an angle changing direction D213 from a user in Step S105. In Step S106 of the image acquisition process of the third time, the bending angle is changed in accordance with the angle changing direction D213. After the change of the bending angle ends, a fourth measurement image I204 is acquired in Step S108 of the image acquisition process of the third time. After the fourth measurement image I204 is acquired, the operation unit 4 accepts an angle changing direction D214 from a user in Step S105. In Step S106 of the image acquisition process of the fourth time, the bending angle is changed in accordance with the angle changing direction D214. After the change of the bending angle ends, a fifth measurement image I205 is acquired in Step S108 of the image acquisition process of the fourth time. Since five measurement images are acquired, it is determined that the number of measurement images reaches the predetermined number in Step S110.

Figure 8:
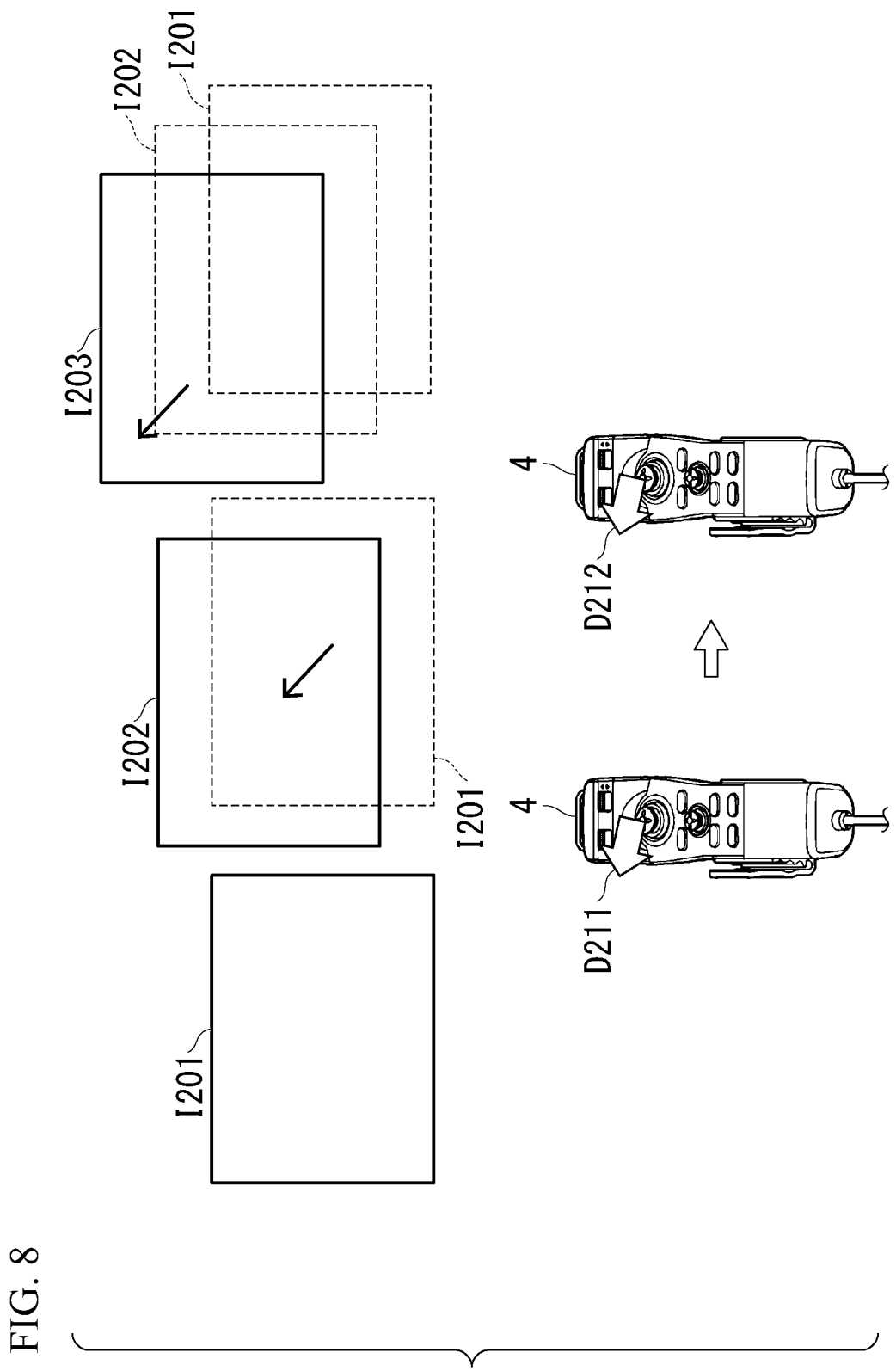
FIG. 8 is a diagram showing the flow of image acquisition according to the first embodiment of the present invention.
Figure 9:
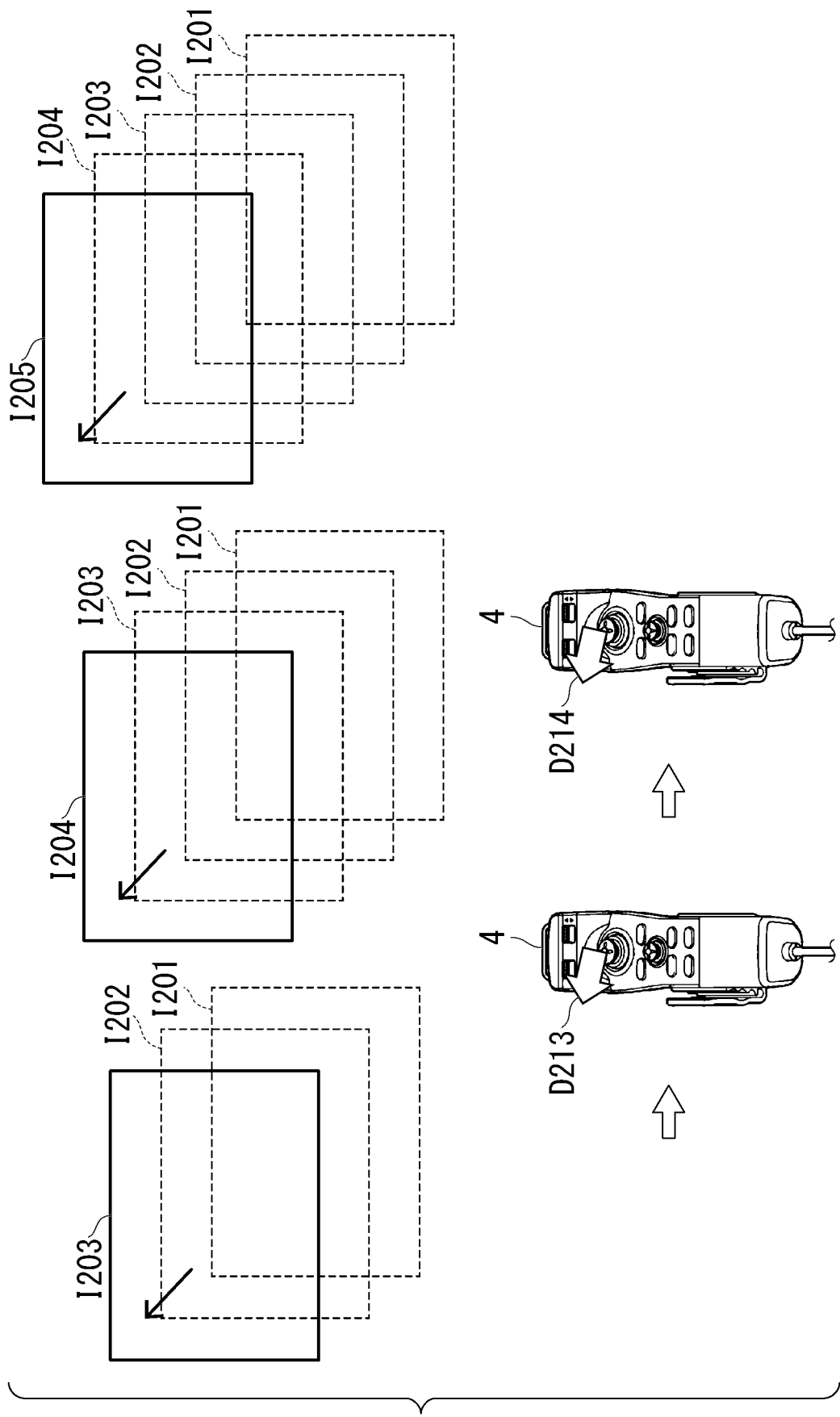
FIG. 9 is a diagram showing the flow of image acquisition according to the first embodiment of the present invention.

In examples shown in FIGS. 8 and 9, the angle changing direction is fixed. However, the angle changing direction is not necessarily fixed all the time in each image acquisition condition.

After Step S111, the display control unit 182 displays the first measurement image acquired in Step S102 on the display unit 5 (Step S112).

After Step S112, a user designates designation points on the displayed first measurement image by operating the operation unit 4. In this way, the user designates a measurement point and a reference point. The operation unit 4 accepts the measurement point and the reference point designated by the user. The designation point setting unit 183 sets the measurement point and the reference point designated by the user on the displayed first measurement image (Step S113).

After Step S113, the user designates a reference distance by operating the operation unit 4. The user designates a length of the reference distance that has already been perceived by the user as a numerical value. The operation unit 4 accepts the reference distance designated by the user. The reference size setting unit 184 sets the reference distance on the displayed first measurement image (Step S114).

For example, the reference distance is a distance between two reference points set on the surface of the subject and is defined using two points. However, the reference distance is not limited to a distance defined using two points. For example, only one reference point may be set on a subject and a distance from the reference point to the endoscope tip end (object distance) may be set as a reference distance. In such a case, the reference distance is defined using only one point.

After Step S114, the measurement unit 186 transforms three-dimensional data of the subject into three-dimensional coordinate data having a dimension of a length (Step S115). At this time, the measurement unit 186 uses the two reference points set in Step S113 and the reference distance set in Step S114.

After Step S115, the measurement unit 186 measures a size defined by measurement points designated by the user using a known measurement method on the basis of the three-dimensional coordinate data acquired in Step S115 (Step S116).

After Step S116, the display control unit 182 displays a result of the measurement on the display unit 5. For example, the result of the measurement is superimposed on the first measurement image displayed on the display unit 5 (Step S117). The result of the measurement may be recorded on an external medium such as a memory card 42. When the process of Step S117 is executed, the measurement process ends.

A method of operating an image acquisition device according to each aspect of the present invention includes first to fifth steps. In a case in which the image acquisition mode is set to the endoscope device 1, the bending control unit 187 recognizes a direction accepted by the operation unit 4 in a first step (Step S105). The reading unit 189 reads first information and second information that define an image acquisition condition in the image acquisition mode from the RAM 14 in a second step (Steps S103 and S104). The first information represents a speed at which the imaging visual field is changed or a distance by which the imaging visual field is changed. The second information represents a timing at which an image used for restoration of a three-dimensional shape is acquired. In a third step (Step S106), the bending control unit 187 causes the bending mechanism 11 to change the imaging visual field at a speed represented by the first information in the recognized direction or change the imaging visual field by a distance represented by the first information in the recognized direction. In a fourth step (Step S108), the image acquisition unit 181 acquires at least two images at timings represented by the second information from the imaging device 28. In a fifth step (Step S111), the three-dimensional shape restoring unit 185 restores the three-dimensional shape of the subject using at least two images acquired from the imaging device 28.

In each aspect of the present invention, the processes of Steps S112 to S117 are not essential.

In the image acquisition mode according to the first embodiment, control of an angle changing direction based on a user's operation and control of the amount of angle change or an angle changing speed executed by the device are combined. For this reason, the endoscope device 1 can shorten a time required for acquiring images for restoration of the three-dimensional shape of the subject. As a result, the inspection efficiency is improved.

Modified Example of First Embodiment

Hereinafter, a modified example of the first embodiment of the present invention will be described.

In the example described above, bending is used for changing the visual point of the endoscope tip end. The changing of the imaging visual field in each aspect of the present invention is not limited to the method using bending. For example, a control jig that can control advancement and retraction of the insertion unit 2 may be used. For example, an optical adapter that can observe a direction perpendicular to the optical axis of the insertion unit 2 is mounted at the tip end 20 of the insertion unit 2. As the insertion unit 2 advances or retracts, the imaging visual field changes. A control jig that can control twist of the insertion unit 2 may be used. A method for changing the imaging visual field is not particularly limited as long as the insertion unit 2 moves in a direction different from the imaging direction.

In the example described above, the operation unit 4 accepts a measurement point and a reference point from the user in Step S113. At this time, the first measurement image acquired in Step S102 is displayed. A measurement image displayed at this time does not need to be the first measurement image. For example, the second measurement image may be displayed. Alternatively, a measurement image that has been acquired last may be displayed. A plurality of acquired measurement images may be displayed, and a user may be able to select a measurement image used for the user to input a designation point from among the plurality of measurement images. In addition, a measurement image for which a reference point is set and a measurement image for which a measurement point is set may be different from each other.

In the example described above, the process of Step S105 is executed in each of a plurality of image acquisition processes until the minimum number of measurement images required for SfM are acquired. The process of Step S105 has only to be executed in at least one image acquisition process. For example, an angle changing direction accepted by the operation unit 4 from the user in Step S105 is stored in the RAM 14. In a case in which a user does not designate a new angle changing direction, the angle changing direction used in the image acquisition process executed at the previous time may be read from the RAM 14. In Step S106, the visual point of the endoscope tip end may be changed on the basis of the angle changing direction read from the RAM 14. A user has only to input a new angle changing direction to the operation unit 4 at a timing at which the angle changing direction is desired to be changed. For this reason, the amount of user's operation can be decreased.

In the example described above, the endoscope device 1 accepts an angle changing direction from a user and changes the bending angle in the angle changing direction. Thereafter, the endoscope device 1 accepts an angle changing direction from the user again and changes the bending angle in the angle changing direction. In other words, the endoscope device 1 repeats acceptance of an angle changing direction and changing of a bending angle. The image acquisition process according to each aspect of the present invention is not limited thereto.

For example, while the endoscope device 1 changes the bending angle in the image acquisition process, the operation unit 4 may accept a new angle changing direction from the user. The endoscope device 1 may update the angle changing direction during the changing of the bending angle and change the bending angle on the basis of the updated angle changing direction. In such a case, a direction in which the endoscope tip end moves is changed during the changing of the bending angle. The amount of the bending angle that has been changed before the angle changing direction is updated is not reset. In other words, after the bending angle is changed, the bending angle is changed only by the amount of a difference. The amount of the difference is a difference between the amount of angle change in the image acquisition process of one time and the amount of change until the angle changing direction is updated.

For example, a case in which a rightward direction is instructed by the user as an angle changing direction, and the amount of angle change read in Step S103 is 100 will be described as an example. For example, after the bending angle is changed by 50, an upward direction is instructed by the user as an angle changing direction. In this case, the endoscope device 1 changes the bending angle by 50 in the upward direction.

In the example described above, while an image acquisition process of one time is executed, the operation unit 4 accepts an angle changing direction from the user, and the bending angle is changed on the basis of the angle changing direction. The angle changing direction may be set in the endoscope device 1 in advance. For example, the endoscope device 1 executes the measurement process shown in FIG. 6 on the basis of a skilled user's operation. At this time, a history of an angle changing direction accepted from a skilled user is stored in the RAM 14. Thereafter, an unskilled general user requests execution of measurement. In Step S105 of the measurement process executed in this case, the angle changing direction stored as the history is read from the RAM 14. While a series of image acquisition processes are executed, the endoscope device 1 changes the bending angle in accordance with the angle changing direction accepted from the skilled user and acquires a measurement image.

The endoscope device 1 can apply the angle changing direction accepted from the skilled user to a measurement process executed on the basis of a general user's instruction. For this reason, the reliability of a result of the process of SfM is easily stabilized regardless of whether or not a user is skilled.

Second Embodiment

In a second embodiment of the present invention, a timing at which the process of acquiring a measurement image is completed can be designated by a user. In a case in which a position desired to be designated by the user as a designation point is relatively close to a region within an imaging visual field on a subject, the configuration of the first embodiment is effective. However, in a case in which a position desired to be designated by the user as a designation point is relatively far from a region within an imaging visual field on a subject, it is necessary to move the endoscope tip end until the position desired to be designated by the user enters the imaging visual field. However, there is a possibility that acquisition of the minimum number of measurement images required for SfM ends while the endoscope tip end is moving. As a result, there is a possibility that the acquisition of measurement images ends before the endoscope tip end reaches a destination. The endoscope device 1 according to the second embodiment has a function of reliably acquiring measurement images including a designation point desired to be designated by a user.

Figure 10:
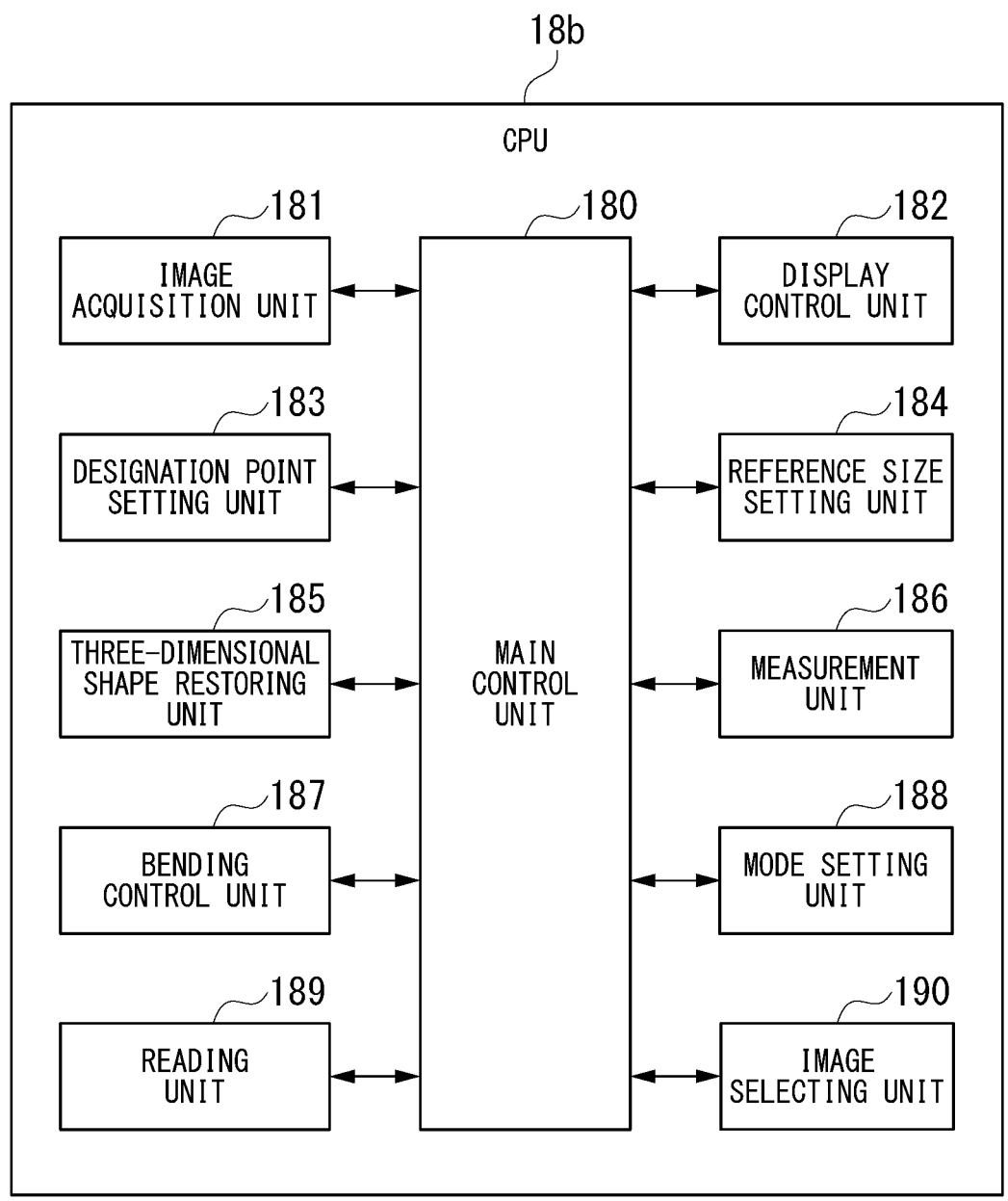
FIG. 10 is a block diagram showing the functional configuration of a CPU according to a second embodiment of the present invention.

In the second embodiment, the CPU 18a shown in FIG. 3 is changed to a CPU 18b shown in FIG. 10. FIG. 10 shows the functional configuration of the CPU 18b. Here, description of components that are the same as those shown in FIG. 3 is omitted.

The CPU 18b includes an image selecting unit 190 in addition to the components described in FIG. 3. After acquisition of measurement images based on an image acquisition condition ends, a main control unit 180 compares a first number with a second number. The first number represents the number of measurement images acquired from an imaging device 28. In the following example, the first number represents the number of measurement images that have been acquired until now. The second number represents the number of measurement images required for restoration of a three-dimensional shape and is at least two. In the following example, the second number represents the minimum number of measurement images required for SfM. In a case in which the first number is the same as the second number, a three-dimensional shape restoring unit 185 restores a three-dimensional shape of the subject.

In a case in which the first number is larger than the second number, the image selecting unit 190 selects at least the second number of measurement images among measurement images acquired from the imaging device 28. In other words, the image selecting unit 190 selects measurement images, the number of which is the same as the second number or more than the second number. In the following example, the image selecting unit 190 selects measurement images, the number of which is required for restoration of a three-dimensional shape. A three-dimensional shape restoring unit 185 restores the three-dimensional shape of the subject using the selected measurement images.

For example, the image selecting unit 190 selects at least the second number of measurement images on the basis of the degree of overlapping between the measurement images acquired from the imaging device 28. Alternatively, the image selecting unit 190 selects the second number of measurement images including a measurement image that has been acquired first among the measurement images acquired from the imaging device 28 and including a measurement image that has been acquired last among the measurement images acquired from the imaging device 28.

In a case in which an operation unit 4 accepts an image acquisition end instruction (an instruction for execution of restoration of a three-dimensional shape) from a user and the first number is smaller than the second number, the operation unit 4 accepts a second direction (an angle changing direction) in which an imaging visual field is changed from the user. The second direction is the same as an angle changing direction accepted from the user at the previous time. Alternatively, the second direction is different from the angle changing direction accepted from the user at the previous time. A bending control unit 187 recognizes the second direction that is accepted by the operation unit 4. The bending control unit 187 causes a bending mechanism 11 to change the imaging visual field at a speed represented by the first information in a recognized second direction again or to change the imaging visual field by a distance represented by the first information in the recognized second direction again. The first information represents a speed at which the imaging visual field is changed (an angle changing speed) or a distance by which the imaging visual field is changed (the amount of angle change). After the imaging visual field is changed in the second direction, the image acquisition unit 181 acquires at least one measurement image from the imaging device 28 at a timing represented by the second information. The second timing represents a timing at which an image used for restoration of a three-dimensional shape is acquired. The first information and the second information define an image acquisition condition in an image acquisition mode (measurement mode).

The endoscope device 1 repeatedly acquires a measurement image on the basis of the image acquisition condition until a sum of a third number and a fourth number becomes the second number. The third number represents the number of measurement images acquired from the imaging device 28 before the operation unit 4 accepts an image acquisition end instruction from the user. The fourth number represents the number of measurement images acquired from the imaging device 28 after the operation unit 4 accepts an image acquisition end instruction from the user.

Figure 11:
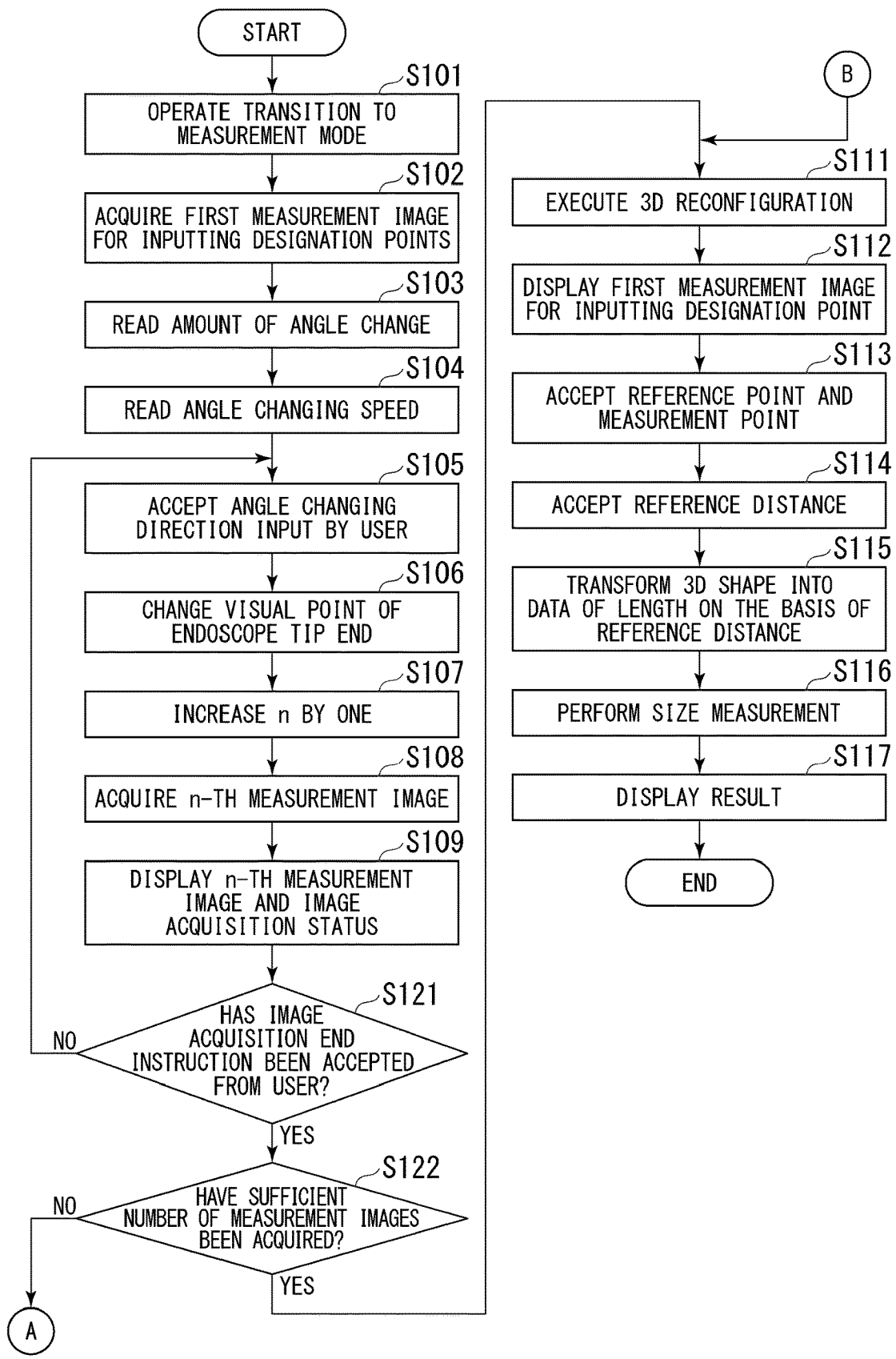
FIG. 11 is a flowchart showing the sequence of a measurement process according to the second embodiment of the present invention.
Figure 12:
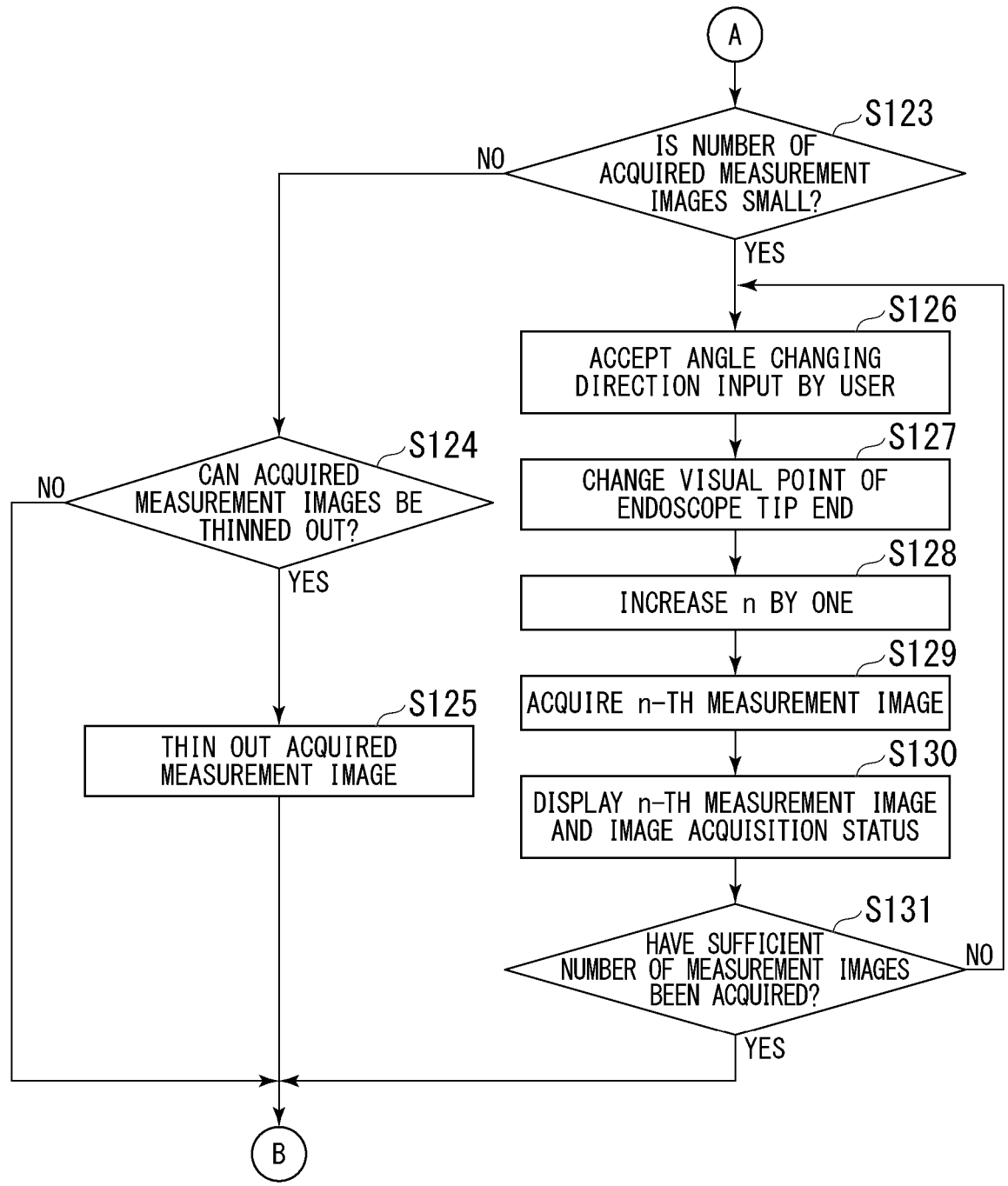
FIG. 12 is a flowchart showing the sequence of a measurement process according to the second embodiment of the present invention.

A measurement process according to the second embodiment will be described with reference to FIGS. 11 and 12. FIGS. 11 and 12 show the sequence of the measurement process. Description of a process that is the same as that shown in FIG. 6 is omitted.

A user determines whether or not a measurement image of a region recognized as a measurement target by the user has been able to be acquired by checking an n-th measurement image displayed in Step S109. In a case in which the user determines that the measurement image of the region has been able to be acquired, the user inputs an image acquisition end instruction to the operation unit 4. The image acquisition end instruction represents an instruction for ending acquisition of a measurement image and executing SfM and restoration of the three-dimensional shape. After Step S109, the operation unit 4 accepts an image acquisition end instruction from a user. The image acquisition end instruction input to the operation unit 4 is input to the CPU 18*b* through a control interface 17. The main control unit 180 determines whether or not an image acquisition end instruction has been accepted from the user (Step S121).

In a case in which the main control unit 180 determines that an image acquisition end instruction has not been accepted from the user in Step S121, the process of Step S105 is executed. In a case in which the main control unit 180 determines that an image acquisition end instruction has been accepted from the user in Step S121, the main control unit 180 compares a variable n with a predetermined number. The variable n represents the number of acquired measurement images. The predetermined number represents the minimum number of measurement images required for SfM. The predetermined number is at least two. The main control unit 180 determines whether or not an appropriate number of measurement images are acquired on the basis of a result of the comparison (Step S122).

In a case in which the variable n is the same as the predetermined number, the main control unit 180 determines that an appropriate number of measurement images have been acquired. In such a case, the process of Step S111 is executed. In a case in which the variable n is different from the predetermined number, the main control unit 180 determines that an appropriate number of measurement images have not been acquired. In such a case, the main control unit 180 determines whether or not the variable n is smaller than the predetermined number (Step S123).

In a case in which a position desired to be designated as a designation point by the user is far from a region within the imaging visual field on a subject, it takes time for the endoscope tip end becomes close to the position. For this reason, a phenomenon in which more than an appropriate number of measurement images are acquired may occur. In a case in which the main control unit 180 determines that the variable n is larger than the predetermined number in Step S123, the image selecting unit 190 determines whether or not the measurement images acquired from the imaging device 28 can be thinned out (Step S124). The thinning out of the measurement images means that the measurement images acquired from the imaging device 28 are classified into images to be used and non-use images. The images to be used are used for 3D reconfiguration including SfM and restoration of the three-dimensional shape. The non-use images are not used for 3D reconfiguration.

In a case in which the image selecting unit 190 determines that the measurement images cannot be thinned out in Step S124, the process of Step S111 is executed. In this case, all the measurement images acquired from the imaging device 28 are used for 3D reconfiguration in Step S111. In Step S124, in a case in which the image selecting unit 190 determines that the measurement images can be thinned out, the image selecting unit 190 thins out the measurement images acquired from the imaging device 28. In this way, the image selecting unit 190 selects only images that are required for SfM as images to be used (Step S125).

The non-use images are measurement images excluding the images to be used from the measurement images acquired from the imaging device 28. The image selecting unit 190 may delete the non-use images. An example of the processes of Step S124 and Step S125 will be described later.

After Step S125, the process of S111 is executed. In this case, measurement images selected by the image selecting unit 190 as the images to be used are used for 3D reconfiguration.

In a case in which the main control unit 180 determines that the variable n is smaller than the predetermined number in Step S123, processes of Steps S126 to S130 are executed. Steps S126 to S130 are respectively the same as Steps S105 to S109.

The operation unit 4 accepts an angle changing direction (second direction) for changing the imaging visual field from the user in Step S126. The bending control unit 187 recognizes the angle changing direction accepted by the operation unit 4 in Step S126. The bending control unit 187 causes the bending mechanism 11 to change the bending angle at an angle changing speed in the recognized angle changing direction by the amount of angle change in Step S127. The image acquisition unit 181 acquires an n-th measurement image from the imaging device 28 in Step S129. The display control unit 182 displays an n-th measurement image on the display unit 5 and displays information representing a progress status related to acquisition of measurement images on the display unit 5 in Step S130.

After Step S130, the main control unit 180 compares a variable n with a predetermined number. The variable n represents the number of acquired measurement images. The predetermined number is the same as the predetermined number used in the process of Step S122. The main control unit 180 determines whether or not the number of acquired measurement images reaches the predetermined number on the basis of a result of the comparison (Step S131).

In a case in which the main control unit 180 determines that the number of acquired measurement images has reached the predetermined number in Step S131, the process of Step S111 is executed. In a case in which the main control unit 180 determines that the number of acquired measurement images has not reached the predetermined number in Step S131, the process of Step S126 is executed.

In a case in which the first number is smaller than the second number, the display control unit 182 may notify that the first number has not reached the second number to the user. For example, before execution of the process of Step S126, the display control unit 182 displays information representing that the number of acquired measurement images is smaller than the minimum number of measurement images required for SfM on the display unit 5. The information includes characters, icons, symbols, or the like. The display control unit 182 may display information representing the number of measurement images required to be additionally acquired on the display unit 5. A notification method for the user is not limited to the display of information using the display unit 5. For example, a voice representing that the first number has not reached the second number may be output.

An example of a process for thinning out images will be described. For example, a method of selecting measurement images on the basis of the degree of overlapping between two or more measurement images acquired from the imaging device 28 may be used. The image selecting unit 190 calculates a ratio of a region common to one measurement image and a measurement image that is acquired two images after the measurement image. For example, a measurement image A, a measurement image B, and a measurement image C are acquired in this order. The image selecting unit 190 calculates a ratio of a region common to the measurement image A and the measurement image C. In a case in which the ratio is higher than a predetermined threshold, the image selecting unit 190 determines that a measurement image acquired between the two measurement images used for the calculation of the ratio of the region can be thinned out. For example, in a case in which the ratio of a region common to the measurement image A and the measurement image C is higher than a predetermined threshold, the image selecting unit 190 determines that the measurement image B can be thinned out. A specific example will be described with reference to FIG. 13.

Figure 13:
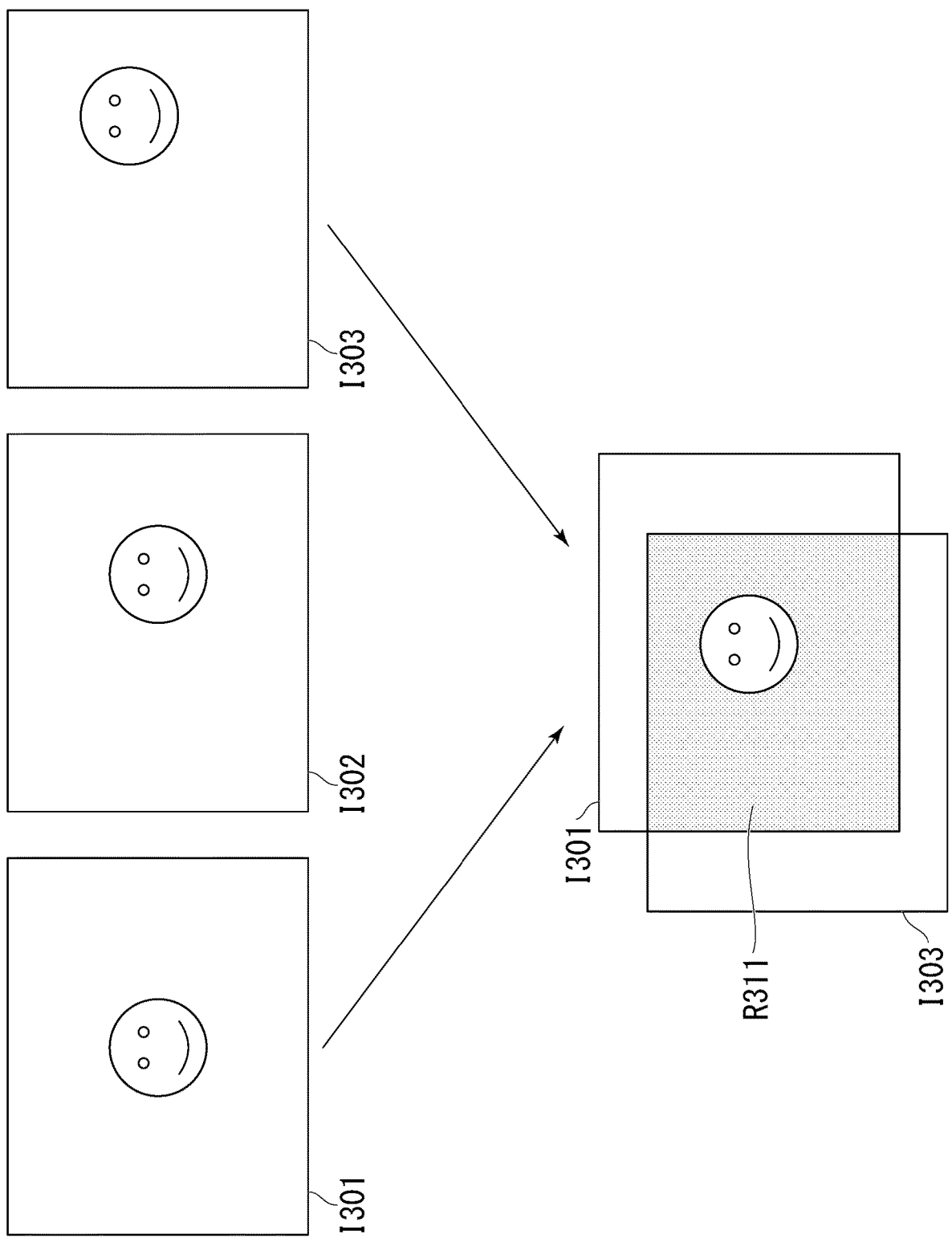
FIG. 13 is a diagram showing measurement images according to the second embodiment of the present invention.

Measurement images acquired from the imaging device 28 include a measurement image I301, a measurement image I302, and a measurement image I303 shown in FIG. 13. After the measurement image I301 is acquired from the imaging device 28, the measurement image I302 is acquired from the imaging device 28. After the measurement image I302 is acquired from the imaging device 28, the measurement image I303 is acquired from the imaging device 28.

The image selecting unit 190 calculates an area (the number of pixels) of a region R311 common to the measurement image I301 and the measurement image I303. Next, the image selecting unit 190 calculates a ratio of the region R311 to the total number of pixels of the image. The total number of pixels of the image is a number acquired by multiplying the number of horizontal pixels by the number of vertical pixels. The image selecting unit 190 compares the calculated ratio with a predetermined threshold. In a case in which the calculated ratio is higher than a predetermined threshold, the image selecting unit 190 determines that the measurement image I302 can be thinned out. In a case in which the calculated ratio is lower than a predetermined threshold, the image selecting unit 190 determines that the measurement image I302 is not thinned out. The endoscope device 1 can decrease the number of measurement images used for SfM by executing the process described above. For this reason, the processing time is shortened.

In a case in which the ratio of the region R311 is higher than a predetermined threshold, the image selecting unit 190 may additionally execute the process of calculating the following two ratios. The image selecting unit 190, as described above, calculates a ratio of a region common to the measurement image I301 and the measurement image I302 and calculates a ratio of a region common to the measurement image I302 and the measurement image I303. In a case in which both the ratios are higher than a predetermined threshold, the image selecting unit 190 may determine that the measurement image I302 can be thinned output.

There are cases in which a region common to the measurement image I301 and the measurement image I303 is large, and a region common to the measurement image I302 and another measurement image is small. In such cases, by executing determination on the basis of only the ratio of the region R311, there is a possibility that the measurement image I302 can be thinned out.

Figure 14:
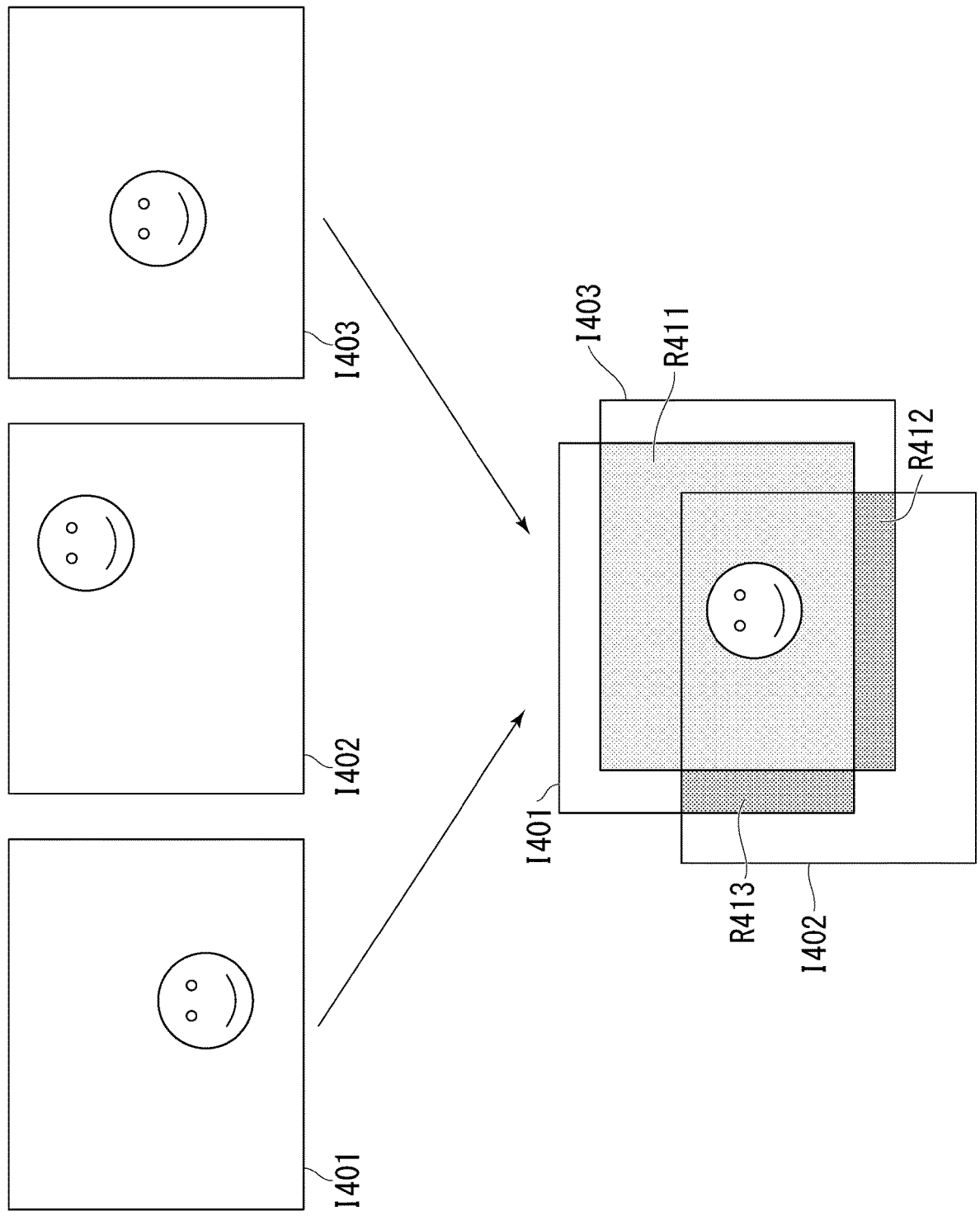
FIG. 14 is a diagram showing measurement images according to the second embodiment of the present invention.

Effects acquired by executing the additional process described above will be described with reference to FIG. 14. The measurement images acquired from the imaging device 28 include a measurement image I401, a measurement image I402, and a measurement image I403 shown in FIG. 14. After the measurement image I401 is acquired from the imaging device 28, the measurement image I402 is acquired from the imaging device 28. After the measurement image I402 is acquired from the imaging device 28, the measurement image I403 is acquired from the imaging device 28.

A region R411 is common to the measurement image I401 and the measurement image I403. A region R412 is common to the measurement image I402 and the measurement image I403 and is not common to the measurement image I401 and the measurement image I402. A region R413 is common to the measurement image I401 and the measurement image I402 and is not common to the measurement image I403 and the measurement image I402. The image selecting unit 190 calculates a ratio of the region R411. In a case in which the additional process is not executed, the image selecting unit 190 determines that the measurement image I402 can be thinned out by only checking that a ratio of the region R411 is higher than a predetermined threshold. After the measurement image I402 is thinned out, the region R412 and the region R413 are not common to the measurement image I401 and the measurement image I403 used for SfM. For this reason, the three-dimensional shape cannot be restored through SfM in the region R412 and the region R413.

In a case in which the additional process described above is executed, the image selecting unit 190 determines that the measurement image I402 is not thinned out by checking that the ratio of at least one of the region R412 and the region R413 is lower than a predetermined threshold. For this reason, the three-dimensional shape can be restored through SfM in the region R412 and the region R413.

The image selecting unit 190 may select at least a measurement image that has been acquired first from the imaging device 28 and a measurement image that has been acquired last from the imaging device 28. For example, first to seventh measurement images are sequentially acquired. After the seventh measurement image is acquired, an image acquisition end instruction is accepted from the user in Step S121. The minimum number of measurement images required for SfM is five. In this case, the image selecting unit 190 may select the first measurement image and the seventh measurement image as images to be used and select three measurement images among the second to sixth measurement images as images to be used.

In a case in which a region focused by the user is included in an image, the user is assumed to cause the operation mode of the endoscope device 1 to proceed from the inspection mode to the measurement mode. For this reason, there is a high possibility that a measurement point or a reference point is designated in a measurement image acquired first from the imaging device 28. Similarly, when a region focused by the user is included in an image, the user is assumed to input an image acquisition end instruction to the operation unit 4. For this reason, there is a high possibility that a measurement point or a reference point is designated in the measurement image acquired last from the imaging device 28. The endoscope device 1 can acquire a measurement image including a region in which a reference distance is desired to be set or a region recognized as a measurement target by the user. For this reason, the inspection efficiency is improved, and the reliability of a process result of the SfM is improved.

Figure 15:
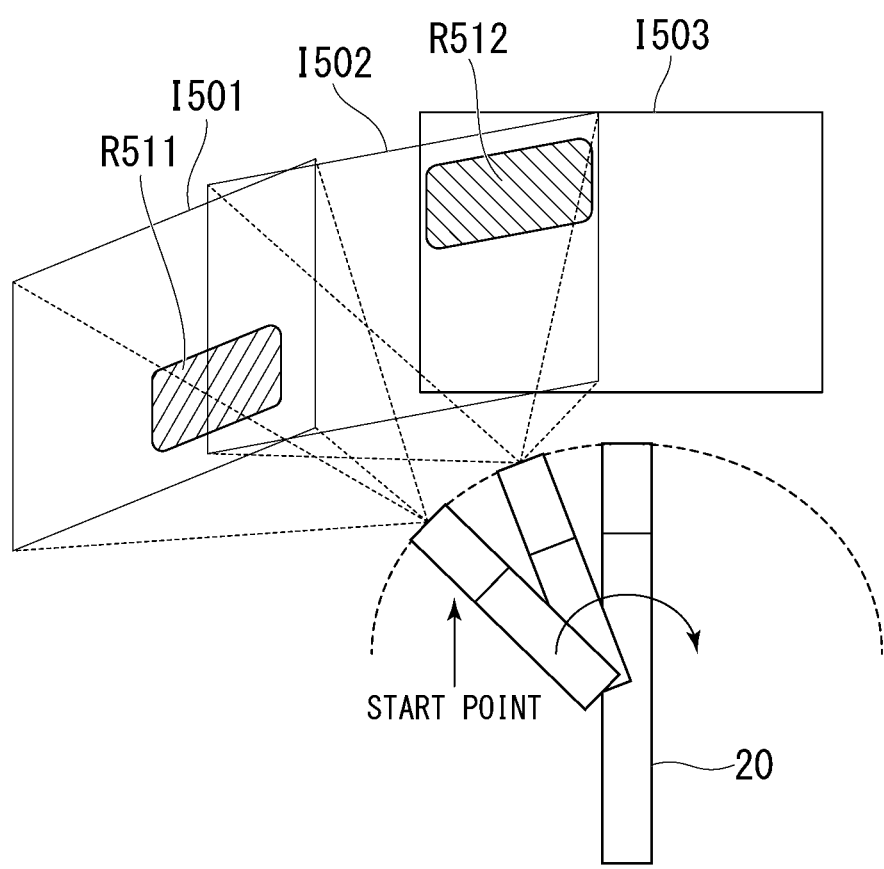
FIG. 15 is a diagram showing movement of a tip end of an endoscope and acquired measurement images according to the second embodiment of the present invention.

An example of the process according to FIGS. 11 and 12 will be described. FIG. 15 shows movement of the endoscope tip end and acquired measurement images until an image acquisition end instruction is accepted from the user in Step S121. For example, when a region R511 is seen in an image, acquisition of a measurement image is started. The region R511 is a region for which the user desires to set a reference distance. In Step S102, a measurement image I501 including the region R511 is acquired. After the measurement image I501 is acquired, the visual point of the endoscope tip end is changed in Step S106 on the basis of an angle changing direction accepted from the user in Step S105. Thereafter, a measurement image I502 is acquired in Step S108. After the measurement image I502 is acquired, similarly, the visual point of the endoscope tip end is changed in Step S106, and a measurement image I503 is acquired in Step S108. At this point, three measurement images are acquired.

The measurement image I503 includes a region R512 that is recognized as a measurement target by the user. The user checks that the region R512 is included in the measurement image I503 and inputs an image acquisition end instruction to the operation unit 4. The main control unit 180 compares the number of acquired measurement images with the minimum number of measurement images required for SfM in Step S122. The number of acquired measurement images is three, and the minimum number of measurement images required for SfM is five. In order to execute SfM, two images are missing, and accordingly, the main control unit 180 determines that the measurement images are insufficient in Step S123.

Figure 16:
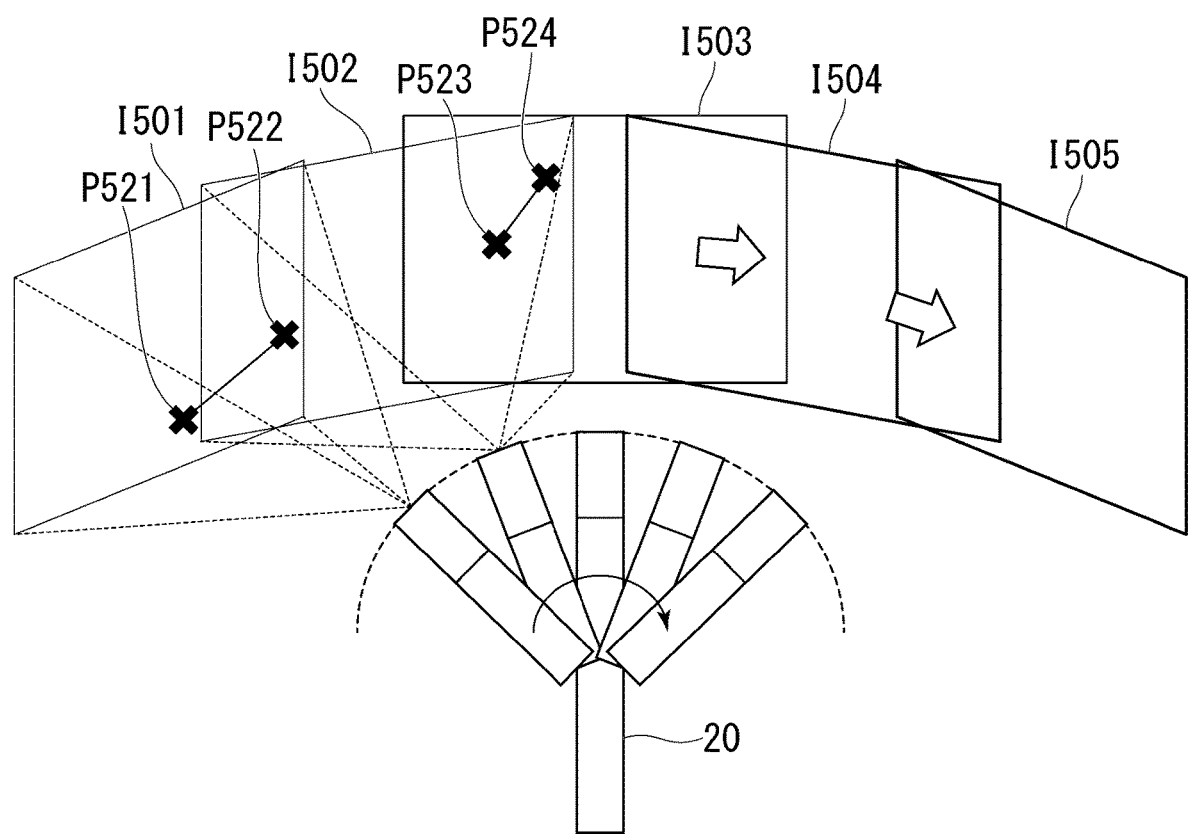
FIG. 16 is a diagram showing movement of a tip end of an endoscope and acquired measurement images according to the second embodiment of the present invention.

FIG. 16 shows movement of an endoscope tip end and acquired measurement images until the minimum number of measurement images required for SfM are acquired. A process used for acquiring a measurement image after an image acquisition end instruction is accepted from a user will be described. In Step S126, a visual point of the endoscope tip end is changed on the basis of an angle changing direction accepted from the user in Step S127. For example, the user instructs the endoscope device 1 about an angle changing direction that is the same as the angle changing direction instructed for acquiring a measurement image I503. Thereafter, a measurement image I504 is acquired in Step S129. After the measurement image I504 is acquired, similarly, the visual point of the endoscope tip end is changed in Step S127, and a measurement image I505 is acquired in Step S129. When the measurement image I505 is acquired, acquisition of the minimum number of measurement images required for SfM ends.

Thereafter, the three-dimensional shape restoring unit 185 executes SfM by executing 3D reconfiguration and restores the three-dimensional shape of the subject in Step S111. The user designates a measurement point and a reference point in Step S113. In the example shown in FIG. 16, a reference point P521 and a reference point P522 are set in a measurement image I501. In the example shown in FIG. 16, a measurement point P523 and a measurement point P524 are set in a measurement image I503.

After an image acquisition end instruction is accepted from the user, two measurement images required for SfM are additionally acquired. For this reason, the reliability of a process result of the SfM is improved.

The endoscope device 1 can acquire the minimum number of measurement images required for the SfM regardless of positional relationships between a reference point and a measurement point designated by the user. As a result, the inspection efficiency is improved, and the reliability of a process result of the SfM is improved.

First Modified Example of the Second Embodiment

In Step S126 shown in FIG. 12, an angle changing direction is accepted from the user. However, the user does not necessarily need to input the angle changing direction to the operation unit 4. When an image acquisition end instruction (an execution instruction of restoration of the three-dimensional shape) is accepted from the user in Step S121, it is assumed that acquisition of measurement images including a region for which the user desires to designate a reference point and a measurement point has been completed. For this reason, the endoscope device 1 has only to acquire insufficient measurement images for the execution of SfM. For such a reason, an endoscope device 1 according to a first modified example of the second embodiment executes control for changing the bending angle instead of the user.

Before the operation unit 4 accepts an image acquisition end instruction from the user, the operation unit 4 accepts an angle changing direction for changing the imaging visual field from the user. The bending control unit 187 recognizes the angle changing direction accepted by the operation unit 4. In a case in which the operation unit 4 accepts an image acquisition end instruction from the user and a first number is smaller than a second number, the bending control unit 187 determines a second direction (angle changing direction) for changing the imaging visual field on the basis of the recognized angle changing direction. The first number represents the number of measurement images acquired from the imaging device 28. In the following example, the first number represents the number of measurement images that have been acquired until now. The second number represents the number of measurement images required for restoration of the three-dimensional shape and is at least two. In the following example, the second number represents the minimum number of measurement images required for the SfM. For example, the second direction is the same as the angle changing direction accepted from the user at the previous time. The bending control unit 187 causes the bending mechanism 11 to change the imaging visual field at a speed represented by first information in a determined second direction again or change the imaging visual field in the determined second direction by a distance represented by the first information again. The first information represents a speed (angle changing speed) for changing the imaging visual field or a distance (the amount of angle change) for changing the imaging visual field. After the imaging visual field is changed in the second direction, the image acquisition unit 181 acquires at least one measurement image at a timing represented by second information from the imaging device 28. The second information represents a timing at which an image used for restoration of the three-dimensional shape is acquired. The first information and the second information define an image acquisition condition in the image acquisition mode (measurement mode).

The endoscope device 1 repeatedly acquires a measurement image on the basis of the image acquisition condition until a sum of a fifth number and a sixth number becomes a second number. Here, the fifth number represents the number of measurement images acquired from the imaging device 28 before the operation unit 4 accepts an image acquisition end instruction from the user. The sixth number represents the number of measurement images acquired from the imaging device 28 after the operation unit 4 accepts an image acquisition end instruction from the user. In an image acquisition process of each time after the operation unit 4 accepts an image acquisition end instruction from the user, the bending control unit 187 determines an angle changing direction on the basis of the angle changing direction previously accepted from the user or the angle changing direction previously determined by the bending control unit 187.

Figure 17:
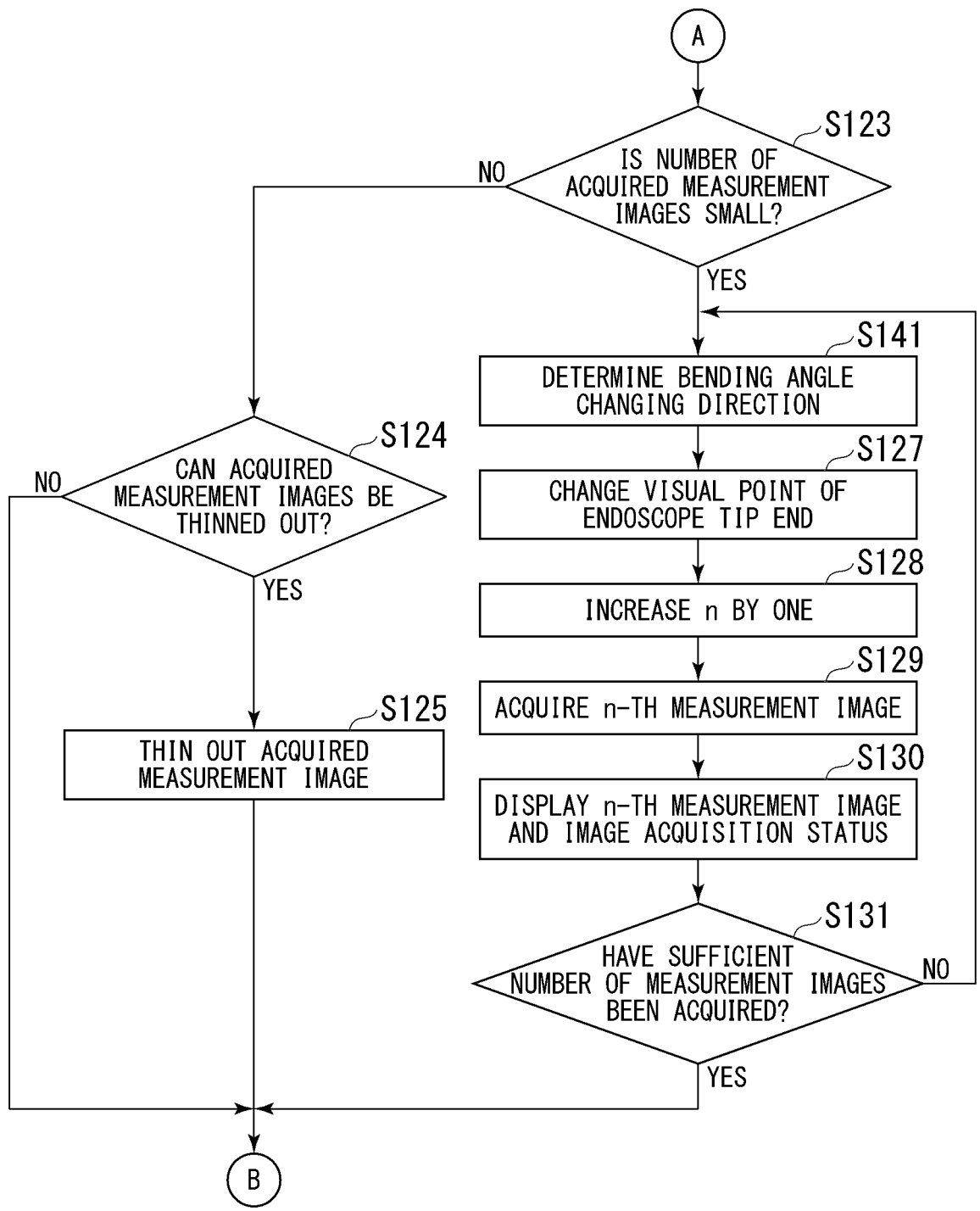
FIG. 17 is a flowchart showing the sequence of a measurement process according to a first modified example of the second embodiment of the present invention.

FIG. 17 shows the sequence of a process executed instead of the process shown in FIG. 12. A process that is the same as the process shown in FIG. 12 is omitted.

Step S126 shown in FIG. 12 is changed to Step S141 shown in FIG. 17. In a case in which the main control unit 180 determines that a variable n is smaller than a predetermined number in Step S123, the bending control unit 187 determines a new angle changing direction on the basis of the angle changing direction accepted from the user in Step S105. For example, the bending control unit 187 determines an angle changing direction used for acquiring an (n+1)-th measurement image on the basis of the angle changing direction accepted from the user for acquiring an n-th measurement image (Step S141). After Step S141, the process of Step S127 is executed.

In a case in which the process of Step S105 is executed a plurality of number of times, a plurality of angle changing directions accepted from the user may be stored in the RAM 14. The bending control unit 187 may determine a new angle changing direction on the basis of a plurality of angle changing directions accepted from the user.

In a case in which the main control unit 180 determines that the number of acquired measurement images has not reached a predetermined number in Step S131, the process of Step S141 is executed. The bending control unit 187 determines a new angle changing direction on the basis of the angle changing direction accepted from the user in Step S105 or the angle changing direction previously determined in Step S141.

Figure 18:
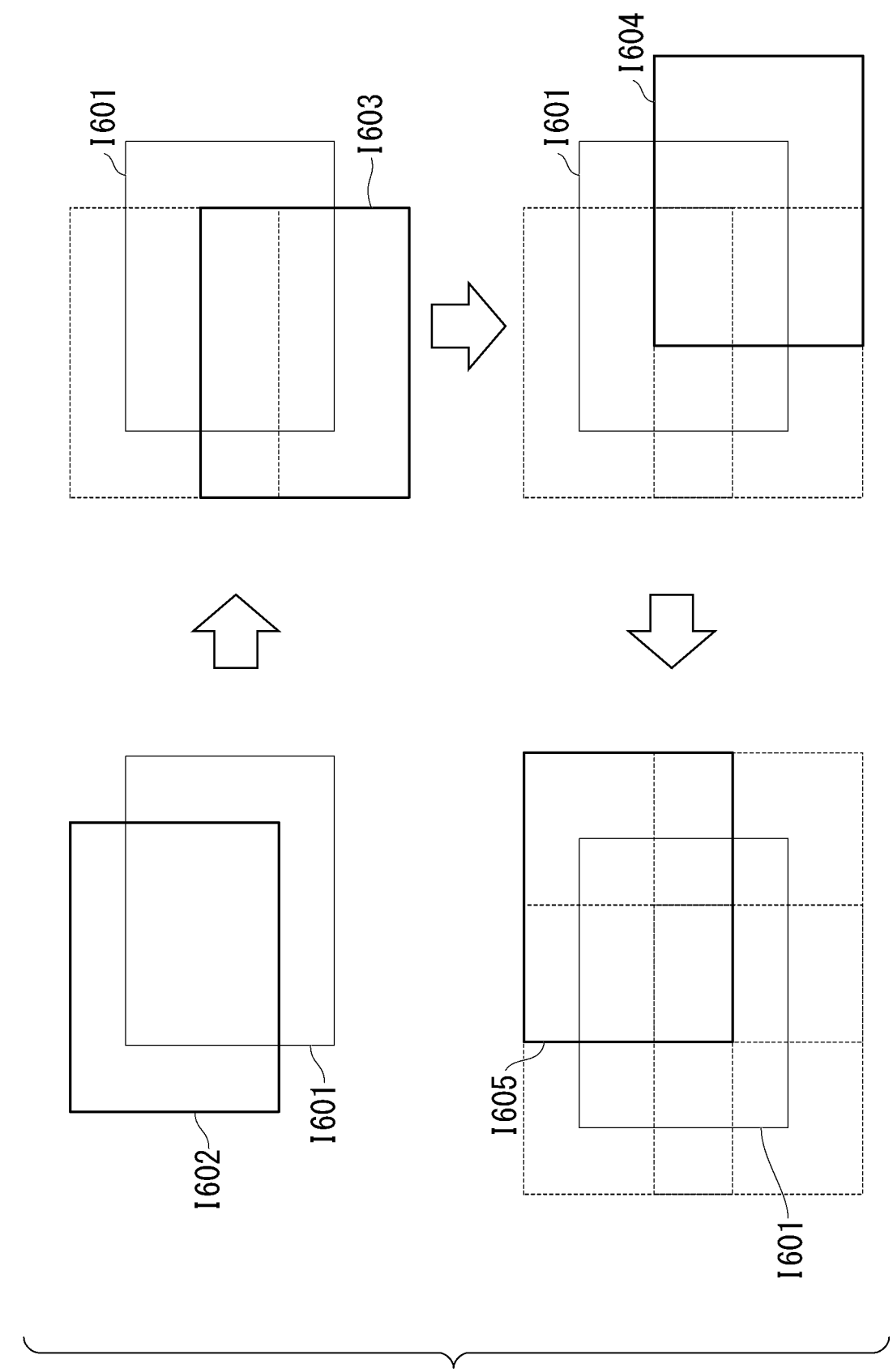
FIG. 18 is a diagram showing measurement images according to the first modified example of the second embodiment of the present invention.

A specific example for controlling an angle changing direction will be described with reference to FIG. 18. FIG. 18 shows measurement images acquired from the imaging device 28. After a measurement image I601 is acquired, an image acquisition end instruction is accepted from the user. The bending control unit 187 determines an angle changing direction used for acquiring a measurement image I602 on the basis of the angle changing direction accepted from the user for acquiring the measurement image I601. For example, the determined angle changing direction is the same as the angle changing direction accepted from the user.

After the measurement image I602 is acquired, the bending control unit 187 determines an angle changing direction used for acquiring a measurement image I603 on the basis of the angle changing direction used for acquiring the measurement image I602. For example, the determined angle changing direction is different from the angle changing direction used for acquiring the measurement image I602.

After the measurement image I603 is acquired, the bending control unit 187 determines an angle changing direction used for acquiring a measurement image I604 on the basis of the angle changing direction used for acquiring the measurement image I603. For example, the determined angle changing direction is different from the angle changing direction used for acquiring the measurement image I603.

After the measurement image I604 is acquired, the bending control unit 187 determines an angle changing direction used for acquiring a measurement image I605 on the basis of the angle changing direction used for acquiring the measurement image I604. For example, the determined angle changing direction is different from the angle changing direction used for acquiring the measurement image I604.

In the example shown in FIG. 18, in order to acquire an image of a peripheral region of a region included in the measurement image I601, the angle changing direction changes in a counterclockwise direction. Four measurement images that have been additionally acquired include a center region of the measurement image I601. The method for controlling the angle changing direction is not limited to the method shown in FIG. 18.

In order to acquire an image of a peripheral region of a region included in the measurement image acquired before an image acquisition end instruction is accepted from the user, the endoscope device 1 controls the angle changing direction. As a result, the number of measurement images including designation points (a measurement point and a reference point) focused by the user can be increased. In a case in which the same designation point is included in many images, the measurement accuracy becomes high. For this reason, the accuracy of size measurement executed after the SfM becomes high.

Second Modified Example of Second Embodiment

In a second modified example of the second embodiment of the present invention, the operation unit 4 and the display unit 5 are integrated or are configured as a touch panel. A user inputs an angular changing direction and a destination to the operation unit 4 by operating the touch panel. The bending control unit 187 causes the bending mechanism 11 to bend the endoscope tip end until the center of the imaging visual field coincides with the destination.

The destination may be a provisional destination used for defining an angle changing direction. For example, the bending control unit 187 causes the bending mechanism 11 to bend the endoscope tip end until the center of the imaging visual field coincides with the provisional destination. Thereafter, the bending control unit 187 causes the bending mechanism 11 to further bend the endoscope tip end with the angle changing direction maintained.

The operation unit 4 accepts a position within the imaging visual field from the user in addition to the angle changing direction. For example, the user touches a position on a measurement image displayed on the display unit 5. At this time, the operation unit 4 accepts the position. The bending control unit 187 recognizes a position accepted by the operation unit 4. First information defining an image acquisition condition represents a speed at which the imaging visual field is changed. The bending control unit 187 causes the bending mechanism 11 to change the imaging visual field at the speed represented by the first information in the recognized bending changing direction until the center of the imaging visual field coincides with the position described above.

The operation unit 4 may simultaneously accepts an angle changing direction and a destination from the user. For example, the operation unit 4, similar to the description presented above, accepts a position on a measurement image displayed on the display unit 5. The center of the measurement image displayed on the display unit 5 is the same as the center of the current imaging visual field. For this reason, the bending control unit 187 can calculate an angle changing direction on the basis of the center of the measurement image and the position on the measurement image accepted from the user.

The user can instruct the endoscope device 1 about a movement destination according to bending. For this reason, the user can easily instruct the endoscope device 1 about the position of the endoscope tip end when a measurement image is acquired.

Third Embodiment

In a third embodiment of the present invention, a user checks whether or not a designation point designated by the user is included in a plurality of measurement images. This checking is executed before execution of SfM. Before the SfM having a high calculation load is executed, the user can check whether or not size measurement can be executed at a measurement point desired to be designated by the user. Before size measurement fails, the endoscope device 1 can urge the user to re-acquire a measurement image in an early stage.

Figure 19:
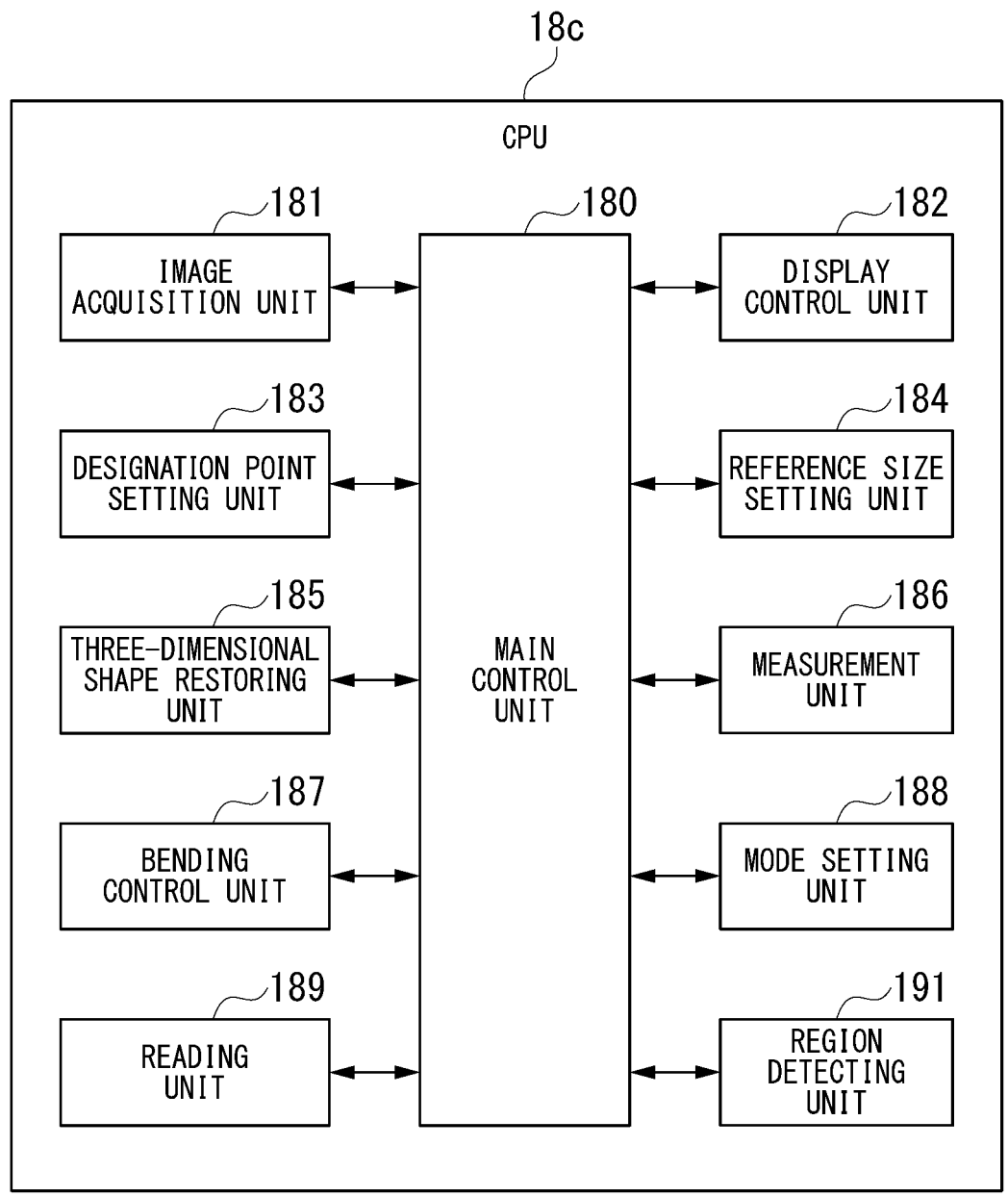
FIG. 19 is a block diagram showing the functional configuration of a CPU according to a third embodiment of the present invention.

In the third embodiment, the CPU 18a shown in FIG. 3 is changed to a CPU 18c shown in FIG. 19. FIG. 19 shows the functional configuration of the CPU 18c. Here, description of components that are the same as those shown in FIG. 3 is omitted.

The CPU 18c includes a region detecting unit 191 in addition to the components described in FIG. 3. Measurement images acquired from the imaging device 28 include one first image and at least one second image. The region detecting unit 191 detects a region overlapping between the first image and the second image. A display control unit 182 enables the region to be visible in the first image by processing the first image. The display control unit 182 displays the processed first image on a display unit 5.

After the first image is displayed on the display unit 5, an operation unit 4 accepts an execution instruction of restoration of a three-dimensional shape from the user. In a case in which the operation unit 4 accepts the execution instruction of restoration of the three-dimensional shape, a three-dimensional shape restoring unit 185 restores the three-dimensional shape of a subject.

Figure 20:
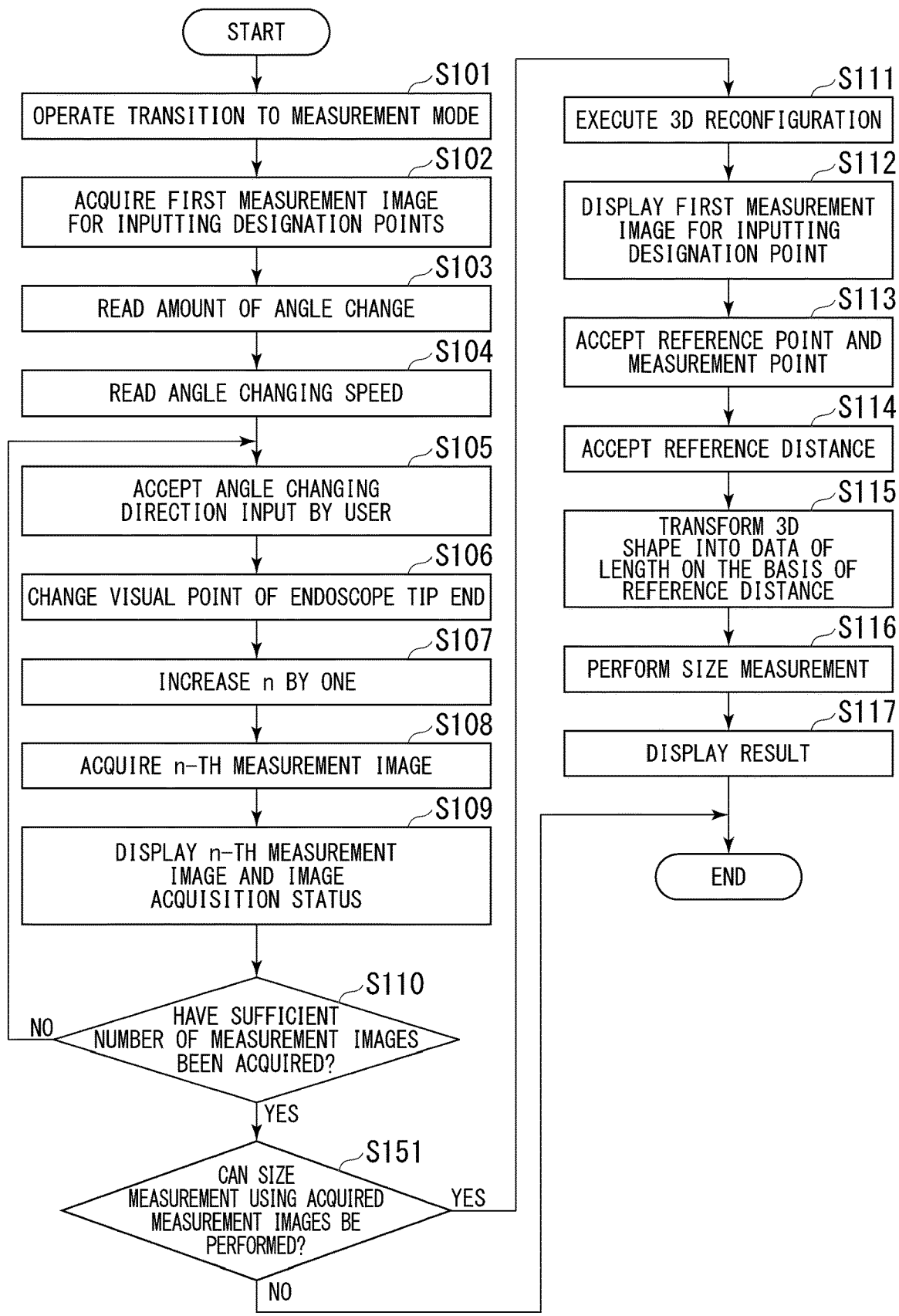
FIG. 20 is a flowchart showing the sequence of a measurement process according to the third embodiment of the present invention.

A measurement process according to the third embodiment will be described with reference to FIG. 20. FIG. 20 shows the sequence of the measurement process. Here, a process that is the same as the process shown in FIG. 6 will not be described.

In a case in which a main control unit 180 determines that the number of acquired measurement images has reached a predetermined number in Step S110, the main control unit 180 determines whether or not size measurement using the acquired measurement images can be performed (Step S151). The user determines whether or not size measurement at a position desired to be designated as a designation point by the user can be performed. More specifically, the user determines whether or not a position desired to be designated as a designation point by the user is included at least two measurement images. The user inputs a result of the determination to the operation unit 4. The operation unit 4 accepts the result of the determination from the user. The result of the determination input to the operation unit 4 is input to the CPU 18c through the control interface 17. The main control unit 180 determines whether or not size measurement using the acquired measurement images can be performed on the basis of the result of the determination input by the user in Step S151.

In a case in which the main control unit 180 determines that size measurement using the acquired measurement images can be performed in Step S151, the process of Step S111 is executed. In a case in which the main control unit 180 determines that size measurement using the acquired measurement images cannot be performed in Step S151, the measurement process ends. In such a case, the operation mode of the endoscope device 1 transitions from a measurement mode to an inspection mode. The user sets a composition for imaging and an imaging condition again and performs an operation for causing the operation mode of the endoscope device 1 to transition from the inspection mode to the measurement mode again. Thereafter, the endoscope device 1 executes a process for acquiring measurement images again.

In a case in which the main control unit 180 determines that size measurement using the acquired measurement images cannot be performed in Step S151, the endoscope device 1 may execute the same process as the process shown in FIG. 12. In this way, the endoscope device 1 can additionally acquire measurement images.

Figure 21:
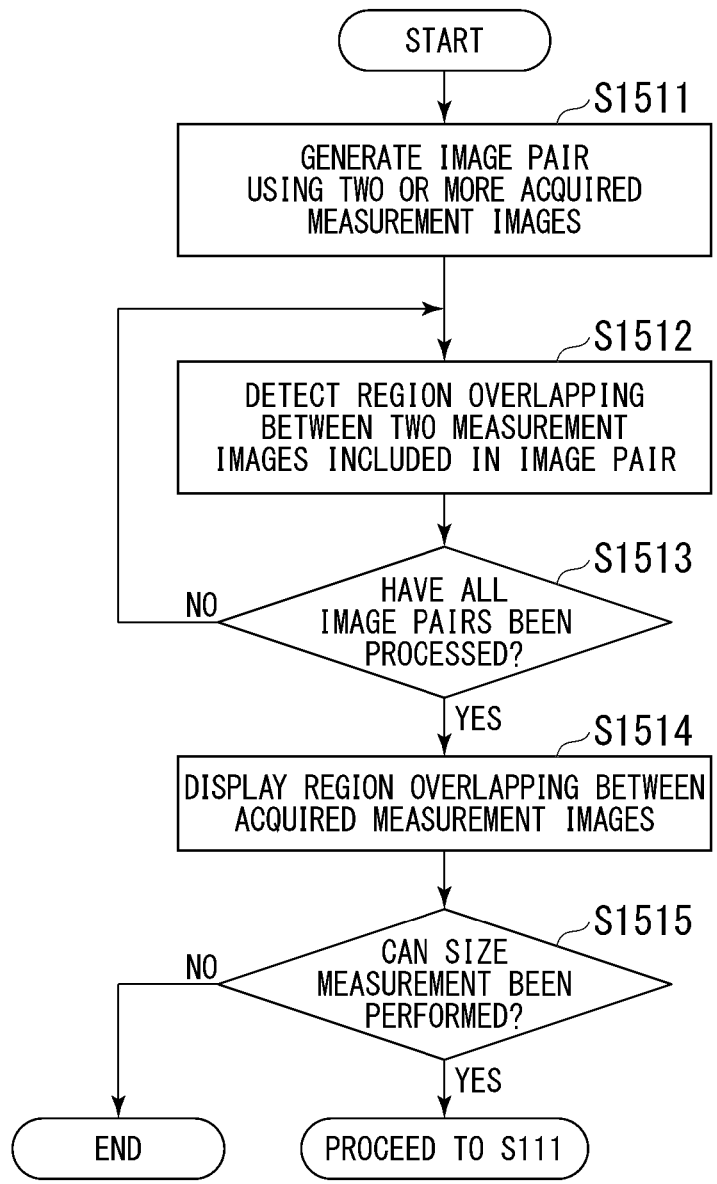
FIG. 21 is a flowchart showing the sequence of a determination process executed in a measurement process according to the third embodiment of the present invention.

Details of Step S151 will be described with reference to FIG. 21. FIG. 21 shows the determination process executed in Step S151.

Figure 22:
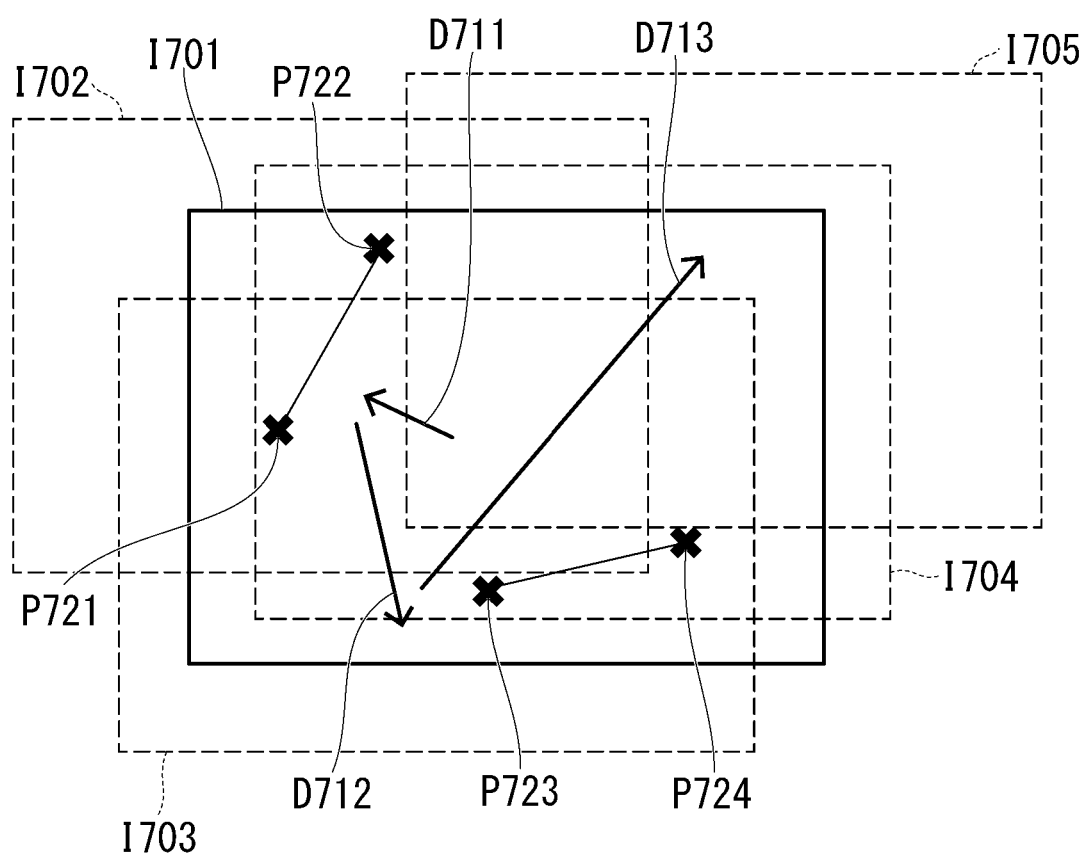
FIG. 22 is a diagram showing measurement images according to the third embodiment of the present invention.

Hereinafter, an example in a case in which five measurement images shown in FIG. 22 are acquired will be described. A measurement image I701 is acquired first. The measurement image I701 includes a region in which a measurement point P721 and a measurement point P722 are desired to be designated by the user. In addition, the measurement image I701 includes a region in which a reference point P723 and a reference point P724 are desired to be designated by the user. The positions of four designation points desired to be designated by the user are shown in FIG. 22. The four designation points include two reference points and two measurement points. When the process of Step S151 is executed, the four designation points shown in FIG. 22 have not been designated yet.

After the imaging visual field is changed in a direction D711, a measurement image I702 is acquired. After the imaging visual field is changed in a direction D712, a measurement image I703 is acquired. After the imaging visual field is changed in a direction D713, a measurement image I704 is acquired. After the imaging visual field is further changed in the direction D713, a measurement image I705 is acquired.

The region detecting unit 191 generates an image pair using two or more measurement images that have been acquired (Step S1511). The image pair includes two measurement images that are different from each other. The image pair includes two measurement images arbitrarily selected from two or more measurement images that have been acquired. Each of the two or more measurement images that have been acquired is included in at least one image pair. For example, one of the two or more measurement images that have been acquired will be defined as a first image. At least one measurement image excluding the first image from the measurement images will be defined as a second image. The image pair includes one first image and one second image. Each of all the second images is included in any one image pair together with the first image. In a case in which the first image of a first image pair and the second image of a second image pair are the same and the second image of the first image pair and the first image of the second image pair are the same, the first image pair and the second image pair are integrated into one image pair. For example, in a case in which five measurement images are acquired, 10 image pairs are generated.

After Step S1511, the region detecting unit 191 selects one image pair and detects a region overlapping between two measurement images included in the selected image pair. In other words, the region detecting unit 191 detects a region overlapping between the first image and the second image (Step S1512). Hereinafter, a region overlapping between two measurement images will be defined as an overlapping region.

After Step S1512, the region detecting unit 191 determines whether or not all the image pairs have been processed. In other words, the region detecting unit 191 determines whether or not the process of Step S1512 has been executed for all the image pairs (Step S1513). In a case in which there is an image pair for which the process of Step S1512 has not been executed, the process of Step S1512 is executed using the image pair.

Figure 23:
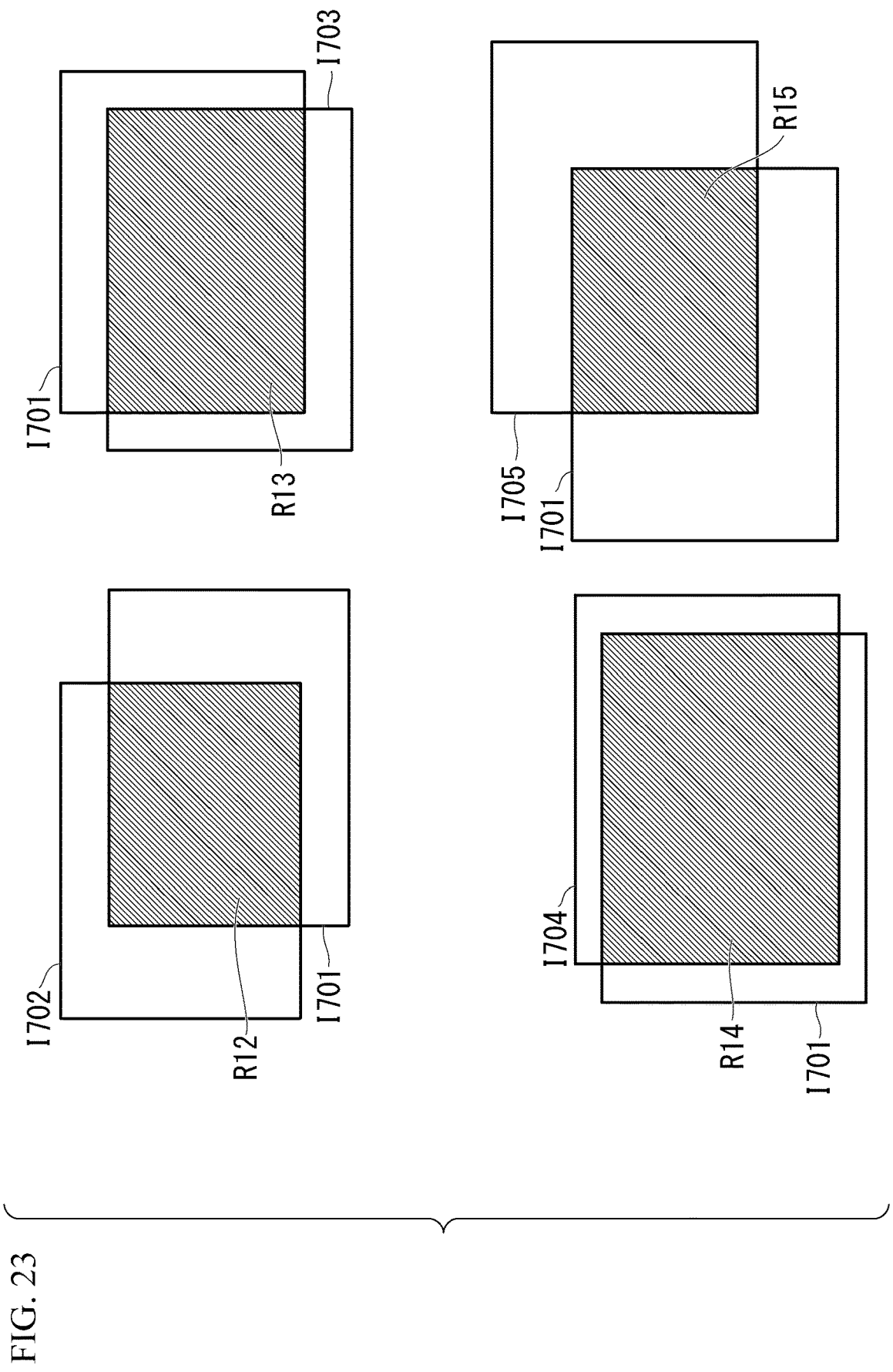
FIG. 23 is a diagram showing measurement images according to the third embodiment of the present invention.

For example, in Step S1512, the region detecting unit 191 detects an overlapping region R12 between a measurement image I701 and a measurement image I702 shown in FIG. 23. Similarly, the region detecting unit 191 detects an overlapping region R13 between the measurement image I701 and a measurement image I703. The region detecting unit 191 detects an overlapping region R14 between the measurement image I701 and a measurement image I704. The region detecting unit 191 detects an overlapping region R15 between the measurement image I701 and a measurement image I705. The region detecting unit 191 repeats the similar process, thereby processing all the image pairs.

In a case in which the region detecting unit 191 determines that all the image pairs have been processed in Step S1513, the display control unit 182 calculates a logical sum of a region overlapping with a region of a different measurement image for each of the measurement images that have been acquired. The display control unit 182 superimposes the region corresponding to the calculated logical sum on each measurement image and displays the measurement image on the display unit 5 (Step S1514).

For example, in the example described above, the display control unit 182 calculates a logical sum for an image pair including the measurement image I701. More specifically, the display control unit 182 calculates logical sums of the overlapping region R12, the overlapping region R13, the overlapping region R14, and the overlapping region R15. Similarly, the display control unit 182 calculates logical sums for image pairs respectively including the measurement image I703, the measurement image I704, and the measurement image I705.

Figure 24:
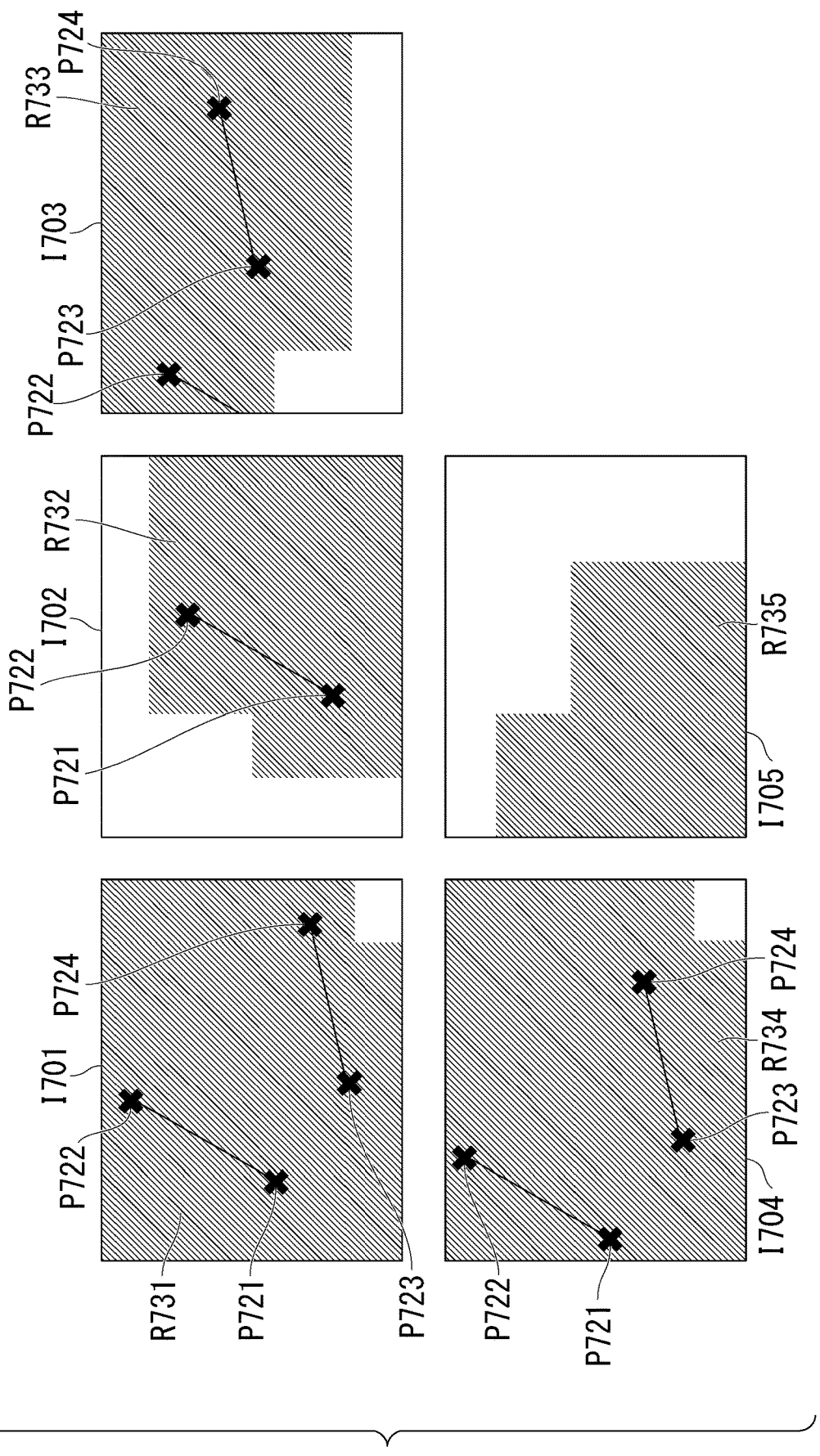
FIG. 24 is a diagram showing images displayed on a display unit according to the third embodiment of the present invention.

FIG. 24 shows each measurement image displayed on the display unit 5 in Step S1514. Each measurement image is a thumbnail image. The region R731 of the measurement image I701, the region R732 of the measurement image I702, the region R733 of the measurement image I703, the region R734 of the measurement image I704, and a region R735 of the measurement image I705 correspond to the logical sums calculated in Step S1514. For example, for the measurement image I701, the first image is the measurement image I701, and the second images are the measurement image I702, the measurement image I703, the measurement image I704, and the measurement image I705. The region R731 includes a region overlapping between the measurement image I701 and a different measurement image. The five measurement images are simultaneously displayed on the display unit 5. The five measurement images may be sequentially displayed on the display unit 5.

The display control unit 182 executes image processing for visually distinguishing a region corresponding to a logical sum from the other regions in each measurement image. For example, the display control unit 182 applies a specific color to the region corresponding to the logical sum. The specific color may be different from the color of the subject. A method of processing a measurement image is not particularly limited as long as a region corresponding to a logical sum and the other regions can be visually distinguished. The display control unit 182 processes the measurement image I701, thereby enabling the region R731 to be visually distinguishable. The display control unit 182, similar to the measurement image I701, processes the measurement image I702, the measurement image I703, the measurement image I704, and the measurement image I705. The display control unit 182 outputs each processed measurement image to the video signal processing circuit 12. The video signal processing circuit 12 outputs each measurement image to the display unit 5. The display unit 5 displays each measurement image.

The positions of the measurement point P721, the measurement point P722, the reference point P723, and the reference point P724 designated by the user are shown in FIG. 24. When each measurement image is displayed on the display unit 5, such designation points have not been set. For this reason, icons of such designation points are not displayed. When each measurement image is displayed on the display unit 5, the user imagines each designation point shown in FIG. 24 on each measurement image.

After Step S1514, the user views each measurement image displayed on the display unit 5 and determines whether or not all the designation points desired to be designated by the user are included in an overlapping region. The user determines whether or not size measurement can be performed and inputs a result of the determination to the operation unit 4. The operation unit 4 accepts the result of the determination from the user. The result of the determination input to the operation unit 4 is input to the CPU 18*c* through the control interface 17. The main control unit 180 determines whether or not the size measurement can be performed on the basis of the result of the determination input by the user (Step S1515).

In a case in which all the positions at which designation points are to be designated are included in the overlapping region of the measurement image, the user determines that size measurement can be performed. In other words, in a case in which all the designation points desired to be designated by the user are included in at least two measurement images, the user determines that size measurement can be performed. In a case in which at least one of the positions at which the designation points are to be designated is not included in the overlapping region, the user determines that size measurement cannot be performed. In other words, in a case in which at least one of the designation points desired to be designated by the user is included only in one measurement image, the user determines that size measurement cannot be performed. In a case in which the user determines that size measurement can be performed, a result of the determination input to the operation unit 4 represents an execution instruction of the SfM and restoration of the three-dimensional shape.

In the example shown in FIG. 24, the measurement point P721 is included in the measurement image I701, the measurement image I702, and the measurement image I704. The measurement point P722 is included in the measurement image I701, the measurement image I702, the measurement image I703, and the measurement image I704. The reference point P723 is included in the measurement image I701, the measurement image I703, and the measurement image I704. Similar to the reference point P723, the reference point P724 is included in the measurement image I701, the measurement image I703, and the measurement image I704.

Each designation point desired to be designated by the user is included in at least two measurement images among the five measurement images that have been acquired. For this reason, the user can determine that size measurement can be performed for the designation points desired to be designated by the user. In a case in which at least one designation point is included in only one measurement image, the user can determine that size measurement for the designation points designated by the user cannot be performed.

In a case in which a designation point is included in at least two measurement images, the designation point is included in an overlapping region. In other words, the designation point is included in at least one of the region R731, the region R732, the region R733, and the region R734. In the example shown in FIG. 24, all the designation points are included in at least one of the region R731, the region R732, the region R733, and the region R734. In other words, all the designation points are included in the overlapping regions. For this reason, the endoscope device 1 can perform size measurement for the designation points desired to be designated by the user on the basis of the five measurement images shown in FIG. 24.

In a case in which the main control unit 180 determines that size measurement can be performed in Step S1515, the process of Step S111 is executed. In such a case, the three-dimensional shape restoring unit 185 executes 3D reconfiguration on the basis of an execution instruction input by the user. In a case in which the main control unit 180 determines that size measurement cannot be performed in Step S1515, the measurement process ends.

Figure 25:
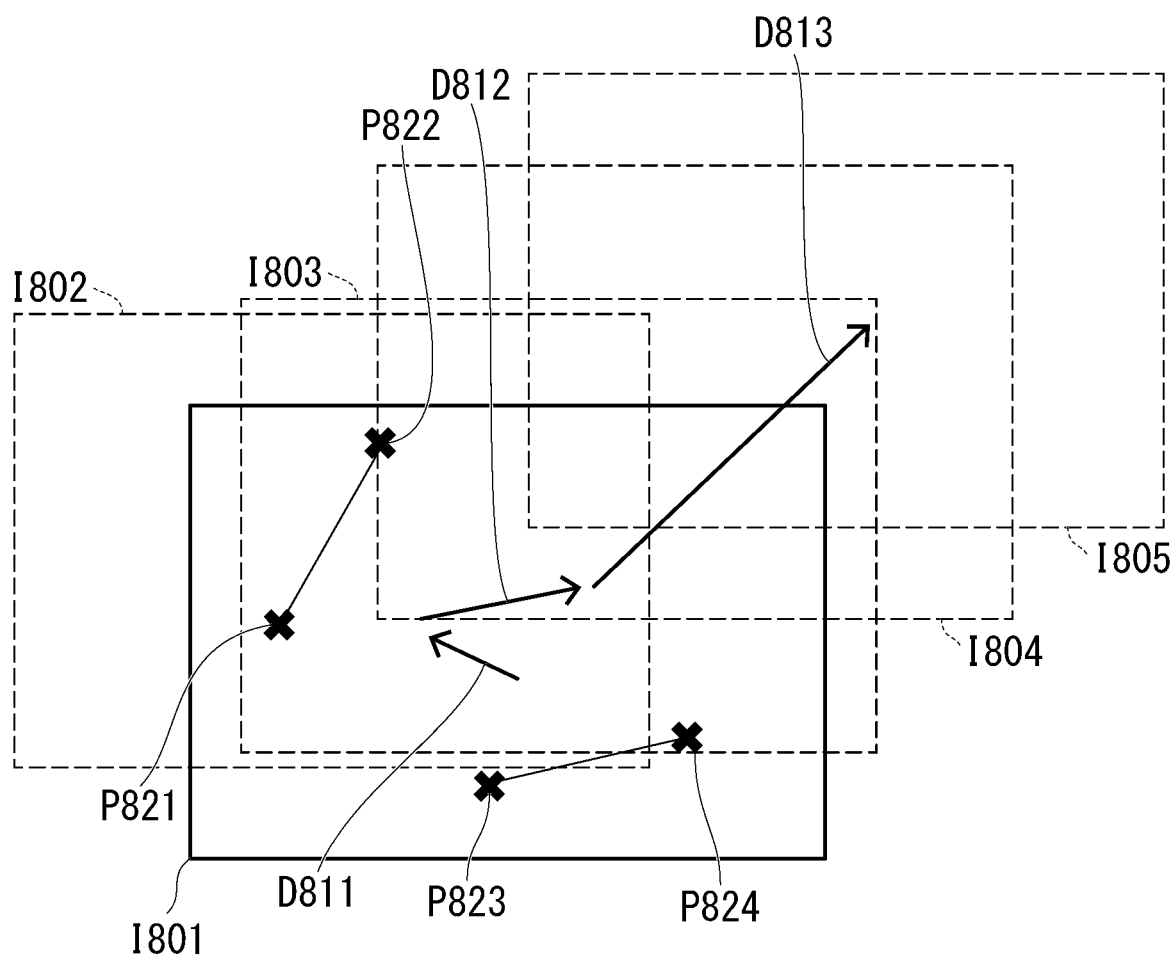
FIG. 25 is a diagram showing measurement images according to the third embodiment of the present invention.

Hereinafter, an example in a case in which the five measurement images shown in FIG. 25 are acquired will be described. A measurement image I801 is acquired first. The measurement image I801 includes a region for which a measurement point P821 and a measurement point P822 are desired to be designated by the user. In addition, the measurement image I801 includes a region for which a reference point P823 and a reference point P824 are desired to be designated by the user. When the process of Step S151 is executed, two reference points and two measurement points shown in FIG. 25 have not been set yet.

After the imaging visual field is changed in a direction D811, a measurement image I802 is acquired. After the imaging visual field is changed in a direction D812, a measurement image I803 is acquired. After the imaging visual field is changed in a direction D813, a measurement image I804 is acquired. After the imaging visual field is further changed in the direction D813, a measurement image I805 is acquired.

Figure 26:
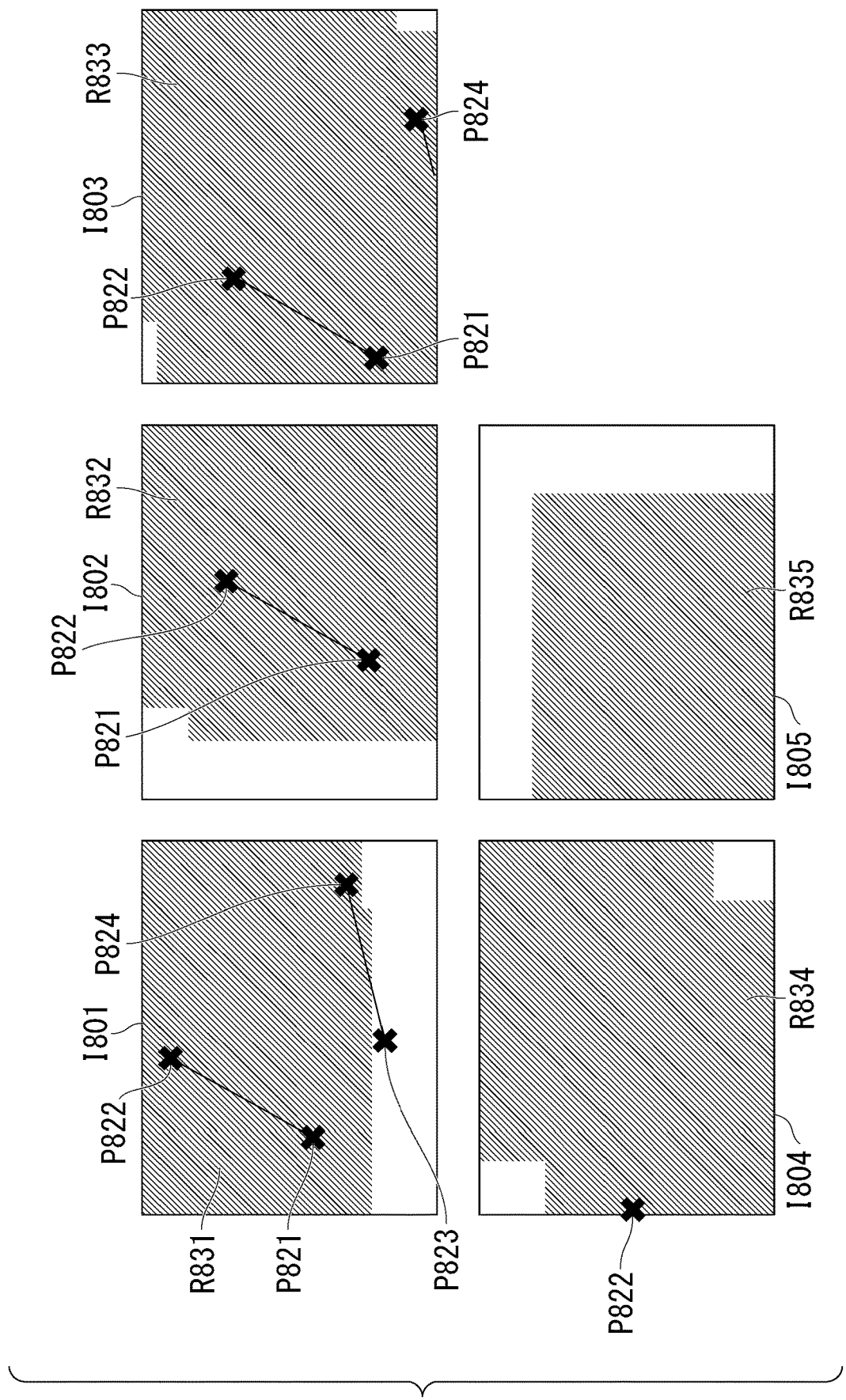
FIG. 26 is a diagram showing images displayed on a display unit according to the third embodiment of the present invention.

FIG. 26 shows each measurement image displayed on the display unit 5 in Step S1514. Each measurement image is a thumbnail image. A region R831 of the measurement image I801, a region R832 of the measurement image I802, a region R833 of the measurement image I803, a region R834 of the measurement image I804, and a region R835 of the measurement image I805 correspond to the logical sums calculated in Step S1514.

In the example shown in FIG. 26, the measurement point P821 is included in the measurement image I801, the measurement image I802, and the measurement image I803. The measurement point P822 is included in the measurement image I801, the measurement image I802, the measurement image I803, and the measurement image I804. The reference point P823 is included only in the measurement image I801. The reference point P824 is included in the measurement image I801 and the measurement image I803.

The reference point P823 is included in only one measurement image I801. For this reason, the reference point P823 is not included in the region R831 of the measurement image I801. The user can determine that size measurement cannot be performed.

In the examples shown in FIGS. 24 and 26, thumbnail images are displayed. The images displayed on the display unit 5 may not necessarily be thumbnail images. Any display method may be used as long as overlapping of regions can be notified to the user.

The endoscope device 1 detects a region overlapping between two measurement images for each image pair and displays measurement images in which the region overlaps on the display unit 5. For this reason, the user can determine whether or not size measurement using a measurement point and a reference point desired to be designated by the user can be performed in a simple manner. In the measurement process shown in FIGS. 20 and 21, the user can determine whether or not size measurement can be performed before SfM having a heavy calculation load is executed. In a case in which at least one of two or more designation points desired to be designated by the user is included in only one measurement image, the endoscope device 1 can urge the user to re-acquire measurement images in an early stage.

A method of displaying the region is not limited to the method of applying a color to the region as long as a region overlapping between two measurement images can be identified by the user. For example, a line surrounding the region may be displayed. In addition, the color of the region that overlaps between measurement images and is displayed is not limited to only one color. For example, measurement accuracy is improved in a region overlapping among three measurement images. For this reason, the endoscope device 1 may display the region in a color different from that of a region overlapping between only two measurement images.

The endoscope device 1 may include the CPU 18a shown in FIG. 3. In such a case, the display control unit 182 displays all the two or more measurement images acquired from the imaging device 28 on the display unit 5. The display control unit 182 does not need to superimpose a region overlapping between two measurement images in the measurement images. The endoscope device 1 supports the user determining whether or not size measurement can be performed by displaying measurement images. However, the endoscope device 1 does not need to perform any other support. The user checks whether or not all the designation points desired to be designated by the user are included in two or more measurement images by viewing the measurement images displayed on the display unit 5. The user determines whether or not size measurement can be performed and inputs a result of the determination to the operation unit 4. The processes executed thereafter are similar to those described above.

Fourth Embodiment

In the third embodiment, a region overlapping between two measurement images, in other words, a region for which size measurement can be performed is visualized by the endoscope device 1. In addition, in the third embodiment, the user determines whether or not designation points designated by the user are included in the visualized region. In the present invention, a subject determining whether or not size measurement can be performed is not limited to a user. In a fourth embodiment of the present invention, an endoscope device 1 determines whether or not size measurement can be performed on the basis of two or more measurement images that have been acquired.

It is difficult for a device to determine whether or not size measurement can be performed for a designation point desired to be designated by the user by using only measurement images without using information input by the user. For this reason, such an example is excluded in the fourth embodiment.

The endoscope device 1 according to the fourth embodiment includes the CPU 18a shown in FIG. 3. Measurement images acquired from an imaging device 28 include one first image and at least one second image. A main control unit 180 determines whether or not a designation point designated by the user in the first image is included in the second image. In a case in which the main control unit 180 determines that the designation point is included in the second image, a three-dimensional shape restoring unit 185 restores the three-dimensional shape of the subject.

Figure 27:
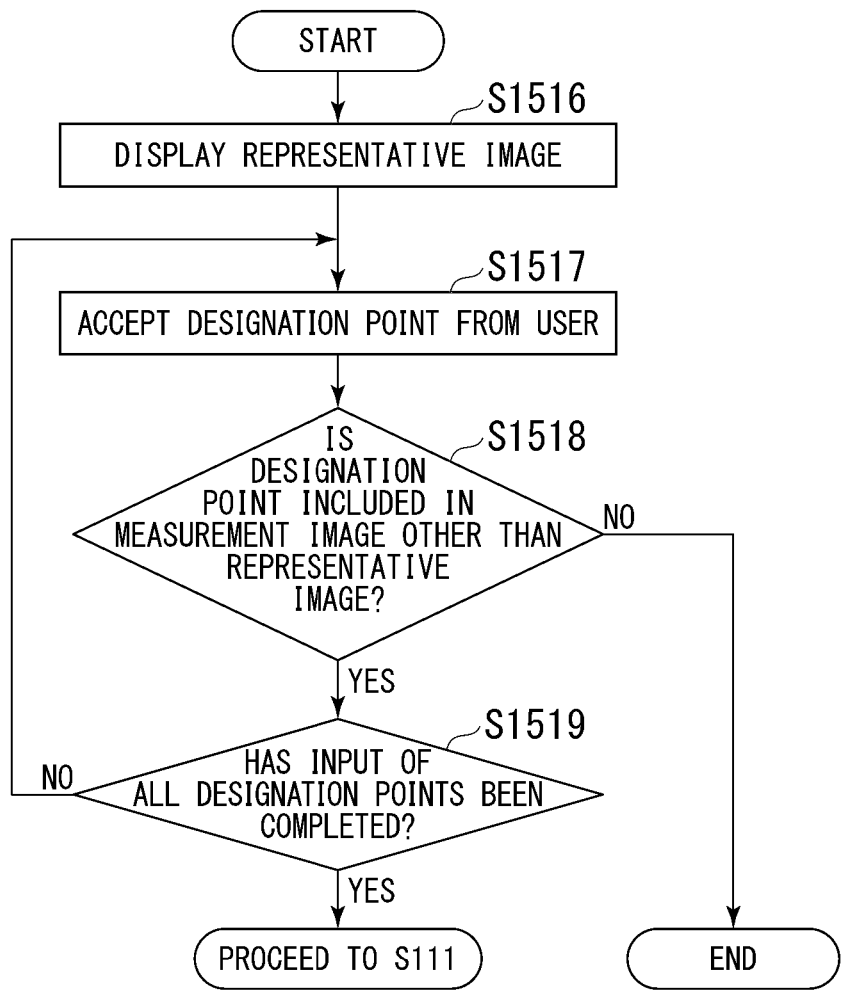
FIG. 27 is a flowchart showing the sequence of a determination process executed in a measurement process according to a fourth embodiment of the present invention.

A measurement process according to the fourth embodiment includes the process shown in FIG. 20. The process shown in FIG. 21 is changed to a process shown in FIG. 27. Details of Step S151 will be described with reference to FIG. 27. FIG. 27 shows a determination process executed in Step S151.

A display control unit 182 displays at least one representative image on the display unit 5 (Step S1516). The representative image may be any image as long as the representative image is an image acquired as a measurement image from the imaging device 28. The display control unit 182 may display a plurality of representative images on the display unit 5.

After Step S1516, the user inputs position information of one designation point in a representative image to the operation unit 4 by operating the operation unit 4. The designation point is a measurement point or a reference point. The operation unit 4 accepts position information from the user. The position information input to the operation unit 4 is input to the CPU 18a through the control interface 17. The main control unit 180 recognizes a designation point accepted from the user on the basis of the position information. The main control unit 180 determines whether or not the designation point accepted from the user is included in a measurement image other than the representative image. In other words, the main control unit 180 determines whether or not a designation point designated by the user in the representative image (first image) is included in a measurement image (second image) other than the representative image. In this way, the main control unit 180 determines whether or not size measurement can be performed (Step S1518).

In Step S1518, the main control unit 180 executes a process for detecting a point similar to the designation point in a measurement image other than the representative image. In a case in which a point similar to the designation point can be detected, the main control unit 180 determines that the designation point is included in a measurement image other than the representative image. In a case in which a point similar to the designation point cannot be detected, the main control unit 180 determines that the designation point is not included in a measurement image other than the representative image.

In a case in which the main control unit 180 determines that the designation point is not included in a measurement image other than the representative image in Step S1518, at least one designation point is included in only one measurement image. For this reason, the main control unit 180 determines that size measurement cannot be performed. In such a case, the measurement process ends, and the operation mode of the endoscope device 1 transitions from the measurement mode to the inspection mode. The user sets a composition for imaging and an imaging condition again and re-performs an operation for causing the operation mode of the endoscope device 1 to transition from the inspection mode to the measurement mode. Thereafter, the endoscope device 1 re-executes a process for acquiring measurement images. In a case in which the main control unit 180 determines that the designation point is not included in a measurement image other than the representative image in Step S1518, the endoscope device 1 may execute the same process as that shown in FIG. 12.

Figure 28:
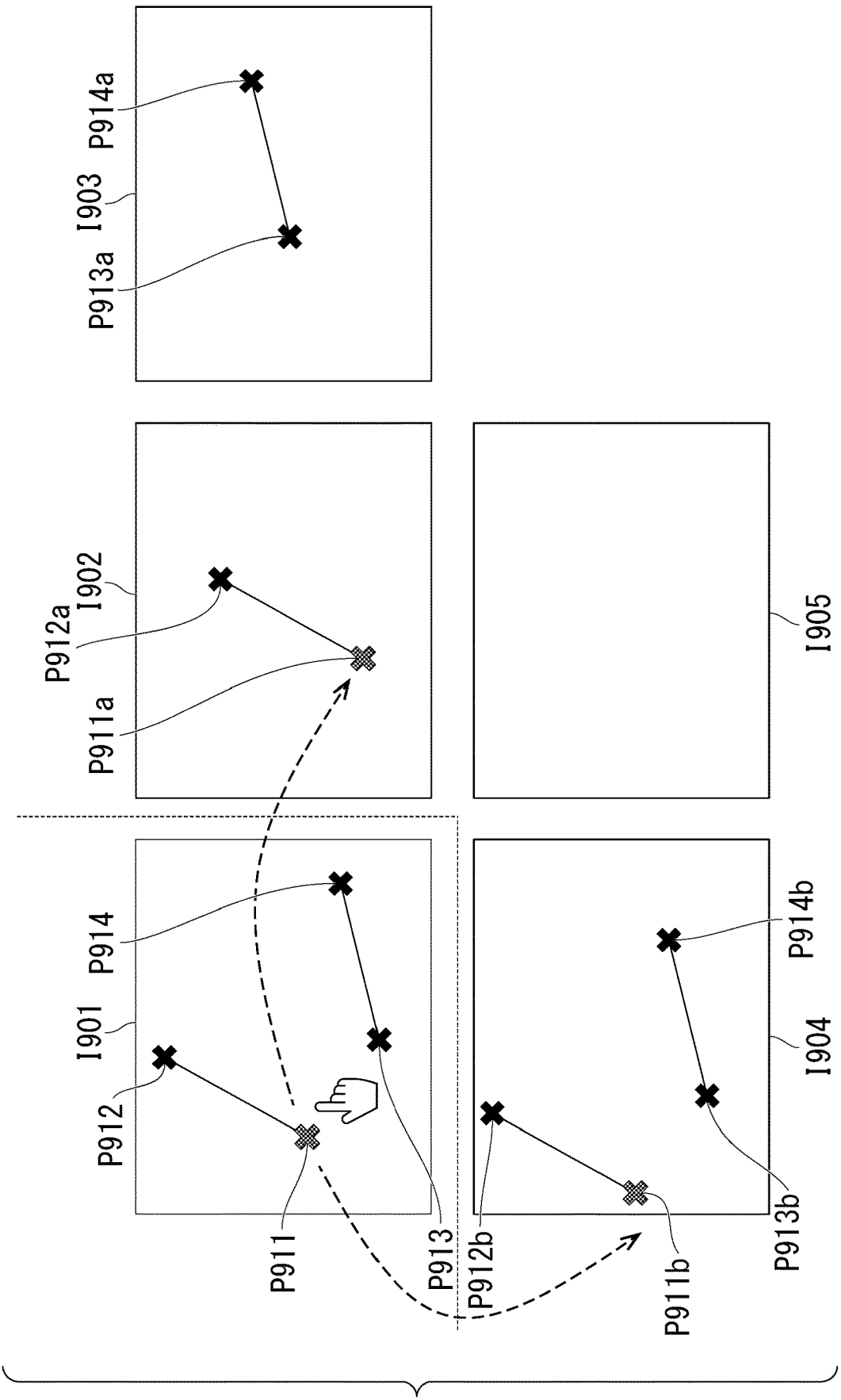
FIG. 28 is a diagram showing measurement images according to the fourth embodiment of the present invention.

A specific process for detecting a point similar to the designation point will be described with reference to FIG. 28. FIG. 28 shows an example of five measurement images acquired from the imaging device 28. A measurement image I901, a measurement image I902, a measurement image I903, a measurement image I904, and a measurement image I905 are acquired from the imaging device 28. The measurement image I901 is a representative image and is displayed on the display unit 5.

For example, in Step S1517, a designation point P911 on the measurement image I901 is accepted from the user. After the designation point P911 is accepted from the user, the main control unit 180 searches for a point similar to the designation point P911 in each of the measurement image I902, the measurement image I903, the measurement image I904, and the measurement image I905. For example, in a search method that can be applied to this, feature quantities of the designation point P911 are described as a multi-dimensional vector. In the search method, coordinates determined as a similar point best coincide with a multi-dimensional vector representing feature quantities of the designation point P911. In each measurement image, in a case in which the degree of coincidence between a point that is the most similar to the designation point P911 and the designation point P911 is equal to or lower than a predetermined threshold, it is determined that a point similar to the designation point P911 is not present in the measurement image.

Visual points at which a plurality of measurement images are acquired are different from each other. For this reason, macroscopic image movement between two measurement images complies with a predetermined rule. In other words, there is a restriction that there is no change in a microscopic positional relationship of the subject between two measurement images. For example, the entire subject moves parallel between two measurement images, or the magnification of the image is changed therebetween. The endoscope device 1 may search for a point similar to the designation point by using this. The search method described above is one of a specific example. The search method is not limited to the method described above. Any search method may be used as long as a point similar to a designation point can be searched.

In the example shown in FIG. 28, a point P911a similar to the designation point P911 is detected in the measurement image I902, and a point P911b similar to the designation point P911 is detected in the measurement image I904. After inputting the designation point P911, the user sequentially inputs the designation point P912, the designation point P913, and the designation point P914.

The main control unit 180 searches for points similar to the designation point P912, the designation point P913, and the designation point P914 in the measurement image I902, the measurement image I903, the measurement image I904, and the measurement image I905. In the example shown in FIG. 28, a point P912a similar to the designation point P912 is detected in the measurement image I902, and a point P912b similar to the designation point P912 is detected in the measurement image I904. A point P913a similar to the designation point P913 is detected in the measurement image I903, and a point P913b similar to the designation point P913 is detected in the measurement image I904. A point P914a similar to the designation point P914 is detected in the measurement image I903, and a point P914b similar to the designation point P914 is detected in the measurement image I904. In the example shown in FIG. 28, all the two or more designation points designated by the user in the representative image are included in measurement images other than the representative image. In other words, all the two or more designation points are included in at least two measurement images.

In a case in which input of designation points ends, the user inputs an input end instruction to the operation unit 4. The operation unit 4 accepts the input end instruction from the user. The input end instruction input to the operation unit 4 is input to the CPU 18a through the control interface 17. In a case in which the main control unit 180 determines that the designation points are included in a measurement image other than the representative image in Step S1518, the main control unit 180 determines whether or not an input end instruction has been accepted from the user. In this way, the main control unit 180 determines whether or not input of all the designation points has been completed (Step S1519).

In a case in which the main control unit 180 determines that an input end instruction has not been accepted from the user in Step S1519, input of designation points has not been completed. In such a case, the process of Step S1517 is executed.

In a case in which the main control unit 180 determines that an input end instruction has been accepted from the user in Step S1519, input of all the designation points has been completed. In such a case, all the designation points are included in at least two measurement images. For this reason, the main control unit 180 determines that size measurement can be performed. In such a case, the process of Step S111 is executed.

The process shown in FIG. 27 includes Step (S1517) in which the user inputs a designation point. For this reason, Step S114 shown in FIG. 20 may be omitted.

A measurement image previously used in the measurement process may be used as a representative image. The representative image includes a designation point set on the basis of position information accepted from the user. The main control unit 180 determines whether or not the designation point set in a representative image is included in a measurement image other than the representative image. In a case in which all the designation points are included in at least one measurement image other than the representative image, the main control unit 180 determines that size measurement can be performed. In a case in which at least one designation point is included only in the representative image, the main control unit 180 determines that size measurement cannot be performed.

The endoscope device 1 determines whether or not the designation point designated by the user is included in a measurement image other than the representative image. In this way, the endoscope device 1 can determined whether or not size measurement using a measurement point and a reference point desired to be designated by the user can be performed. In the measurement process shown in FIGS. 20 and 27, before the SfM having a heavy calculation load is executed, the user can determine whether or not size measurement can be performed. In a case in which at least one of two or more designation points desired to be designated by the user is included only in one measurement image, the endoscope device 1 can urge the user to re-acquire measurement images in an early stage.

The endoscope device 1 may execute the process of Step S1517 instead of execution of the process of Step S114 shown in FIG. 20. In such a case, only the order of the process is changed, and an increase in the entire processing load is inhibited.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An image acquisition device comprising:
an image sensor configured to generate images on the basis of an optical image of a subject within an imaging visual field;
a visual field changing unit that changes the imaging visual field by moving at least the image sensor;
an operation unit that accepts a direction in which the imaging visual field is changed from a user; and
a controller comprising hardware, the controller being configured to:
recognize the direction accepted by the operation unit in a case in which an image acquisition mode used for acquiring the images used for restoration of a three-dimensional shape of the subject is set in the image acquisition device,
read first information and second information that define image acquisition conditions in the image acquisition mode from a storage medium, the first information representing a speed at which the imaging visual field is changed or a distance by which the imaging visual field is changed, and the second information representing timings at which the images used for restoration of the three-dimensional shape are acquired,
cause the visual field changing unit to change the imaging visual field at the speed represented by the first information in the recognized direction or change the imaging visual field by the distance represented by the first information in the recognized direction,
acquire at least two of the images at the timings represented by the second information from the image sensor, and
restore the three-dimensional shape using the images acquired from the image sensor.

2. The image acquisition device according to claim 1, wherein:
the images acquired from the image sensor include one first image and at least one second image, and
the controller is configured to:
detect a region that overlaps between the first image and the second image,
cause the region in the first image to be visibly distinguishable from other regions in the first image by processing the first image, and
display the processed first image on a display.

3. The image acquisition device according to claim 2, wherein:
the operation unit accepts an execution instruction of restoration of the three-dimensional shape from the user after the first image is displayed on the display, and
the controller is configured to restore the three-dimensional shape in a case in which the operation unit accepts the execution instruction.

4. The image acquisition device according to claim 1, wherein:
the images acquired from the image sensor include one first image and at least one second image, and
the controller is configured to:
determine whether or not a designation point designated by the user in the first image is included in the second image, and
restore the three-dimensional shape in a case in which the control unit determines that the designation point is included in the second image.

5. The image acquisition device according to claim 1, wherein, after acquisition of the images based on the image acquisition conditions ends, the controller is configured to compare a first number with a second number, the first number representing the number of the images acquired from the image sensor, and the second number representing the number of the images required for restoration of the three-dimensional shape and is at least two.

6. The image acquisition device according to claim 5, wherein the controller is configured to:
select at least the second number of the images among the images acquired from the image sensor in a case in which the first number is larger than the second number, and
restore the three-dimensional shape using the selected images.

7. The image acquisition device according to claim 6, wherein the controller is configured to select at least the second number of the images on the basis of a degree of overlapping between the images acquired from the image sensor.

8. The image acquisition device according to claim 6, wherein the controller is configured to select the second number of the images that include an image that has been acquired first among the images acquired from the image sensor and include an image that has been acquired last among the images acquired from the image sensor.

9. The image acquisition device according to claim 5, wherein:
in a case in which the operation unit accepts an image acquisition end instruction from the user and the first number is smaller than the second number, the operation unit accepts a second direction in which the imaging visual field is changed from the user, and
the controller is configured to:
recognize the second direction accepted by the operation unit,
cause the visual field changing unit to change the imaging visual field again at the speed represented by the first information in the recognized second direction or change the imaging visual field again by the distance represented by the first information in the recognized direction, and
acquire at least one of the images from the image sensor at the timing represented by the second information after the imaging visual field is changed in the second direction.

10. The image acquisition device according to claim 5, wherein:
in a case in which the operation unit accepts an image acquisition end instruction from the user and the first number is smaller than the second number,
the controller is configured to:
determine a second direction in which the imaging visual field is changed on the basis of the recognized direction,
cause the visual field changing unit to change the imaging visual field at the speed represented by the first information in the determined second direction again or change the imaging visual field by the distance represented by the first information in the determined second direction again, and acquire at least one of the images from the image sensor at the timing represented by the second information after the imaging visual field is changed in the second direction.

11. The image acquisition device according to claim 5, wherein the controller is configured to notify the user that the first number has not reached the second number in a case in which the first number is smaller than the second number.

12. The image acquisition device according to claim 1, wherein:

the operation unit accepts the direction by accepting a position within the imaging visual field from the user, the first information represents the speed at which the imaging visual field is changed; and the controller is configured to:

recognize the direction on the basis of the position accepted by the operation unit, and cause the visual field changing unit to change the imaging visual field at the speed represented by the first information in the recognized direction until a center of the imaging visual field coincides with the position.

13. The image acquisition device according to claim 1, wherein the controller is configured to:

display at least one of the images acquired from the image sensor on a display, and count a first number and displays information representing a ratio of the first number to a second number on the display, the first number representing the number of the images acquired from the image sensor, and the second number representing the number of the images required for restoration of the three-dimensional shape and is at least two.

14. The image acquisition device according to claim 1, wherein the controller is configured to:

generate thumbnail images by decreasing the number of pixels of the images acquired from the image sensor, and display the thumbnail images on a display.

15. A method of operating an image acquisition device, the device including:

an image sensor that generates images on the basis of an optical image of a subject within an imaging visual field;

a visual field changing unit that changes the imaging visual field by moving at least the image sensor;

an operation unit that accepts a direction in which the imaging visual field is changed from a user; and a controller, the method comprising:

recognizing the direction accepted by the operation unit in a case in which an image acquisition mode used for acquiring the images used for restoration of a three dimensional shape of the subject is set in the image acquisition device;

reading first information and second information that define image acquisition conditions in the image acquisition mode from a storage medium, the first information representing a speed at which the imaging visual field is changed or a distance by which the imaging visual field is changed, and the second information representing timings at which the images used for restoration of the three-dimensional shape are acquired;

causing the visual field changing unit to change the imaging visual field at the speed represented by the first information in the recognized direction or change the imaging visual field by the distance represented by the first information in the recognized direction;

acquiring at least two of the images at the timings represented by the second information from the image sensor, and restoring the three-dimensional shape using the images acquired from the image sensor.

\* \* \* \* \*